(12) United States Patent
Hostetler et al.

(10) Patent No.: US 6,599,887 B2
(45) Date of Patent: Jul. 29, 2003

(54) METHODS OF TREATING VIRAL INFECTIONS USING ANTIVIRAL LIPONUCLEOTIDES

(75) Inventors: Karl Y. Hostetler, Del Mar, CA (US); Raj Kumar, San Diego, CA (US); Louise M. Stuhmiller, Rancho Santa Fe, CA (US)

(73) Assignee: Chimerix, Inc., San Diego, CA (US)

( * ) Notice: Subject to any disclaimer, the term of this patent is extended or adjusted under 35 U.S.C. 154(b) by 0 days.

(21) Appl. No.: 09/846,398

(22) Filed: May 1, 2001

(65) Prior Publication Data

US 2001/0033862 A1 Oct. 25, 2001

Related U.S. Application Data

(63) Continuation of application No. 08/483,148, filed on Jun. 7, 1995, now abandoned, which is a division of application No. 08/415,769, filed on Apr. 3, 1995, now Pat. No. 6,448,392, and a continuation of application No. 08/040,499, filed on Mar. 31, 1993, now abandoned, which is a continuation of application No. 07/373,088, filed on Jun. 28, 1989, now Pat. No. 5,223,263, which is a continuation-in-part of application No. 07/319,485, filed on Mar. 6, 1989, now abandoned, which is a continuation-in-part of application No. 07/216,412, filed on Jul. 7, 1988, now abandoned.

(51) Int. Cl.$^7$ ............................................. A61K 31/7052
(52) U.S. Cl. ............................. 514/47; 514/48; 514/51; 514/52; 536/26.1; 536/26.5
(58) Field of Search ............................. 514/47, 48, 51, 514/52; 536/26.1, 26.5

(56) References Cited

U.S. PATENT DOCUMENTS

| | | | |
|---|---|---|---|
| 4,283,394 A | 8/1981 | West et al. | |
| 4,291,024 A | 9/1981 | Turcotte | |
| 4,429,008 A | 1/1984 | Martin et al. | |
| 4,464,359 A | 8/1984 | Suhadolnik et al. | |
| 4,471,113 A | 9/1984 | MacCoss | |
| 4,533,254 A | 8/1985 | Cook et al. | |
| 4,579,849 A | 4/1986 | MacCoss | |
| 4,605,645 A | 8/1986 | Watanabe et al. | |
| 4,622,392 A | 11/1986 | Hong et al. | |
| 4,670,424 A | 6/1987 | MacCoss | |
| 4,692,433 A | 9/1987 | Hostetler | |
| 4,737,323 A | 4/1988 | Martin et al. | |
| 4,797,479 A | 1/1989 | Shuto et al. | |

(List continued on next page.)

FOREIGN PATENT DOCUMENTS

| | | |
|---|---|---|
| EP | 0 056 265 | 7/1982 |
| EP | 0 122 151 | 10/1984 |
| EP | 0 199 451 | 10/1986 |
| EP | 0 254 268 | 1/1988 |
| EP | 0 262 876 | 4/1988 |
| EP | 0 302 760 | 8/1988 |
| EP | 0 286 418 | 12/1988 |
| EP | 0 306 597 | 3/1989 |
| EP | 0 311 100 | 4/1989 |
| GB | 2 168 353 A | 12/1985 |
| GB | A-2168350 | 6/1986 |
| JP | 59-250306 | 11/1984 |
| JP | 60-65284 | 3/1985 |
| JP | 61-59072 | 3/1986 |
| JP | 61-110456 | 5/1986 |
| JP | 62-41263 | 2/1987 |
| JP | 62-182423 | 7/1987 |
| WO | WO 89/01776 | 2/1985 |
| WO | WO 88 07532 | 10/1988 |
| WO | 89 02 733 | 6/1989 |
| WO | WO 90/00555 | 1/1990 |
| WO | 91/09602 | 7/1991 |
| WO | 91/18914 | 12/1991 |
| WO | 91/19726 | 12/1991 |
| WO | 92/03462 | 3/1992 |
| WO | 93/16091 | 8/1993 |
| WO | 93/16092 | 8/1993 |
| WO | 94/03465 | 2/1994 |
| WO | 94/25046 | 11/1994 |

OTHER PUBLICATIONS

Nasr, Mohamed et al., "Computer–assisted structure–activity correlations of dideocynucleoside analogs as potential anti–HIV drugs (mini–review)", Antiviral Research, 14:125–148 (1990).

(List continued on next page.)

*Primary Examiner*—Francisco Prats
(74) *Attorney, Agent, or Firm*—Swanson & Bratschun, LLC

(57) ABSTRACT

Compounds are disclosed for treating AIDS, herpes, and other viral infections by means of lipid derivatives of antiviral agents. The compounds consist of nucleoside analogues having antiviral activity which are linked, commonly through a phosphate group at the 5' position of the pentose residue, to one of a selected group of lipids. The lipophilic nature of these compounds provide advantages over the use of the nucleoside analogue alone. It also makes it possible to incorporate them into the lamellar structure of liposomes, either alone or combined with similar molecules. In the form of liposomes, these antiviral agents are preferentially taken up by macrophages and monocytes, cells which have been found to harbor the target HIV virus. Additional site specificity may be incorporated into the liposomes with the addition of ligands, such as monoclonal antibodies or other peptides or proteins which bind to viral proteins. Effective nucleoside analogues are dideoxynucleosides, azidothymine (AZT), and acyclovir; lipid groups may be glycolipids, sphingolipids, phospholipids or fatty acids. The compounds persist, after intracellular hydrolysis, as phosphorylated or non-phosphorylated antiviral nucleosides. The compounds are effective in improving the efficacy of antiviral nucleoside analogues by prolonging the antiviral activity after the administration of the drug has ended, and in preventing retroviral replication in HIV infections which have become resistant to therapy with conventional forms of the antiretroviral agents.

11 Claims, 3 Drawing Sheets

U.S. PATENT DOCUMENTS

| | | | |
|---|---|---|---|
| 4,810,697 A | 3/1989 | Speiser et al. | |
| 4,867,973 A | 9/1989 | Goers et al. | |
| 4,921,951 A | 5/1990 | Shuto | |
| 4,963,662 A | 10/1990 | Matthes et al. | |
| 4,997,926 A | 3/1991 | Haertle | |
| 5,026,558 A | 6/1991 | Hwang | |
| 5,039,667 A | 8/1991 | Tyrrell et al. | |
| 5,153,180 A | 10/1992 | Matthes et al. | |
| 5,194,654 A | 3/1993 | Hostetler et al. | |
| 5,223,263 A | 6/1993 | Hostetler et al. | |
| 6,030,960 A | 2/2000 | Morris-Natschke | |

OTHER PUBLICATIONS

Nasr, Mohamed et al., "Computer–assisted structure–activity correlations of halodideocynucleoside analogs as potential anti–HIV drugs", AIDS Research and Human Retroviruses, 8:135–144 (1992).

Hostetler et al., International Conference on AIDS, p. 536, Th.co.o. 18 (abs.) (1989).

Lehninger, Biochemistry 2nd ed., Worths Publishers, Johns Hopkins University, pp. 291–294 (1975).

Hess, G. et al., Inhibition of Hepatitis B Virus Deoxyribonucleic Acid Polymerase . . . , Antimicrobial Agents and chemotherapy, 19(1):44–50 (1981).

Kassanides, C. et al., Inhibition of Duck Hepatitis B Virus Replication . . . , Gastroenterology, 97:1275–1280 (1989).

Lee, B. et al., in Vitro and In Vivo Comparison of the Abilities of Purine . . ., Antimicrobial Agents and Chemotherapy, 33:336–339 (1989).

Matthes, E. et al., Potent Inhibition of Hepatitis B Virus Production in Vitro . . . , Antimicrobial Agents and Chemotherapy, 34:1986–1990 (1990).

Sherpof, G.L. et al., In Vivo Uptake and Processing of Liposomes . . . , NATO ASI Series Ser. A: Targeting Drugs, 155:109–120 (1988).

Spanjer, H. et al., Intrahepatic Distribution of Small Unilamellar Liposomes . . . , Biochem. Biophys. Acta, 863:224–230 (1986).

Yoshikawa, M. et al., A Novel Method for Phosphorylation of Nucleosides to 5'–nucleotides, Tetrahedron Lett, 50:5065–5068 (1967).

Yoshikawa, M. et al., Studies of Phosphorylation III, Selective Phosphorylation . . . , Bull. Chem. Soc. Japan, 42:3205–3208 (1967).

Berdel et al., Antineoplastic Activity of Conjugates of Lipids and 1–B–D–arabinofuranosylcytosine, Lipids, 22(11):943–946 (1987).

Hostetler et al., Synthesis and Antiretroviral Activity of Phospholipid Analogs of Azidothymidine and Other Antiviral Nucleosides, J. Biol. Chem., 265(11):6112–6117 (1990).

Ryu, Ross, Matsushita, MacCoss, Hong and West, Phospholipid–Nucleoside Conjugates. 3. Syntheses and Preliminary Biological Evaluation of 1–β–D–Arabinofuranosylcytosine 5'–Monophosphate–L–1,2–Dipalmitin and Selected Darabinofuranosylcytosine 5'–Diphosphate–L–1,2–Diacylglycerols, J. Med. Chem. 25:1322–1329 (1982).

Bennett, Jr., Shannon, Allan and Arnett, Studies on the Biochemical Basis For the Antiviral Activities of some Nucleoside Analogs, Annals New York Academy of Sciences, 255:342–358 (1975).

Montgomery, The Design of Chemotherapeutic Agents, Accounts of Chemical Research 19:293–300 (1986).

DeClercq, Balzarini, Descamps and Eckstein, Antiviral, Antimetabolic and Antineoplastic Activities of 2'–or 3'–amino or –asido–substituted deoxyribonucleosides, Biochemical Pharmacology, 29:1849–1851 (1980).

Price, Banerjee and Acs, Inhibition of the Replication of Hepatitis B Virus by the Carbocyclic Analogue of 2'–deoxyguanosine, Proc. Natl. Acad. Sci. USA 86:8541–8544. (1989).

Scherphof, Daemen, Spanjer and Roerdink, Liposomes in Chemo–and Immunotherapy of Cancer, Lipids 22(11): 891–896 (1987).

Yang, Turcotte and Steim, Biophysical Properties of Cytidine Diphosphate Diacylglycerol in Solution, Biochimica et Biophysica Acta 834:364–375 (1985).

Hantz, Allaudeen, Ooka, DeClercq and Trepo, Inhibition of Human dn Woodchuck Hepatitis Virus DNA Polymerase by the Triphosphates of Acyclovir, 1–(2'–deoxy–2'–fluoro–β–D–arabinofuranosyl)–5–iodocytosine and E–5–(2–bromovinyl)–2'–deoxyuridine, Antiviral Research 4:187–199 (1984).

Matsushita, Ryu, Hong and MacCoss, Phospholipid Derivatives of Nucleoside Analogs as Prodrugs with Enhanced Catabolic Stability, Cancer Research 41:2707–2713 (1981).

Agranoff et al. Cytidine Diphosphate–DL–Dipalmitin, Biochemical Preparations 10:47–51 (1963).

Alving, Steck, Chapman, Jr., Waits, Hendricks, Swartz, Jr. and Hanson, Therapy of Leishmaniasis: Superior Efficacious of Liposome–Encapsulated Drugs, Proc. Natl. Acad. Sci. USA 75:2959–2963 (1978).

Bangham et al. (1965) Diffusion of Univalent Ions Across the Lamellac of Swollen Phospholipids, J. Mol. Biol. 13:238–252.

Benjamins and Agranoff, Distribution and Properties of CDP–Diglyceride:Inositol Transferase From Brain, J. Neurochemistry 16:513–527 (1969).

Black and Watson, The Use of Pentostam Liposomes in the Chemotherapy of Experimental Leishmaniasis, Transactions of the Royal Society of Tropical Medicine and Hygiene 71:550–552 (1977).

Bligh and Dyer, A Rapid Method of Total Lipid Extraction and Purification, Canadian Journal of Biochemistry and Physiology 37:911–917 (1959).

Brown, D.A. et al., An X–ray examination of long–chain alkyl dihydrogen phosphates and dialkyl hydrogen phosphates and their sodium salts, J. Chem. Soc. (London), pp. 1584–1588 (1955).

Cao, O, Choy and Chan, Regulation by Vitamin E of Phosphatidylcholine Metabolism in Rat Heart, Biochem. J. 247:135–140 (1987).

Carman and Fischl, Modification of the Agranoff–Suomi method of the synthesis of CDP–Diacylglycerol, J. of Food Biochemistry 42:53–59 (1980).

Fischl, Richman, Grieco, Gottilieb, Volberding, Laskin, Leedom, Groopman, Mildvan, Schooley, Jackson, Durack, Phil, King, The Efficacy of Azidothymidine (AZT) in the Treatment of Patients with Aids and Aids–Related Complex, The New England Journal of Medicine 317:185–191 (1987).

Fukunaga, Miller, Hostetler and Deftos, Liposome Entrapment Enhances the Hypocalcemic Action of Parenterally Administered Calcitonin, Endocrinology 115:757–761 (1984).

Heath, Lopez, Piper, Montgomery, Stern and Papahadjopoulos, Liposome–mediated Delivery of Pteridine Antifolates to Cells in Vitro: Potency of Methotrexate, and its a and ? Substituents, Biochimica et Biophysica Acta 862:72–80 (1986).

Herman, Rahman, Ferrans, Vick and Schein, Prevention of Chronic Doxorubicin Cardiotoxicity in Beagles By Liposomal Encapsulation, Cancer Research 43:5427–5432 (1983).

Ho and Neil, Pharmacology of 5'–Esters of 1–β–D–Arabinofuranosylcytosine, Cancer Research 37:1640–1643 (1977).

Huang, A., Huang, L. and Kennel, Monoclonal Antibody Covalently Coupled with Fatty Acid, J. Biological Chemistry 255:8015–8018 (1980).

Kende, Alving, Rill, Swartz, Jr. and Canonico, Enhanced Efficacy of Liposome–Encapsulated Ribavirin Against Rift Valley Fever Virus Infection in Mice, Antimicrobial Agents and Chemotherapy 27:903–907 (1985).

Koenig, Gendelman, Orenstein, Dal Canto, Pezeshkpour, Yungbluth, Janotta, Aiksamit, Martin and Fauci, Detection of AIDS Virus in Macrophages in Brain Tissue from AIDS Patients with Encephalopathy, Science 233:1089–1093 (1986).

Kim et al. (1983) Preparation of Multivesicular Liposomes, Biochimica et Biophysica Acta, 728:339–348.

Leserman, Barbet and Kourilsky, Targeting to Cells of Fluorescent Liposomes Covalently Coupled with Monoclonal Antibody or Protein A, Nature 288:602–604 (1980).

Lopez–Berestein, Liposomal Amphotericin B in the Treatment of Fungal Infections, Ann. Int. Med. 105:130–131 (1986).

MacCoss, Ryu and Matsushita, The Synthesis, Characterization, and Preliminary Biological Evaluation of 1–β–D–Arabinofuranosylcytosine–5'-Diphosphate–L–1, 2–Dipalmitin, Biochemical and Biophysical Research Communications 85:714–723 (1978).

Martin, Tippie, McGee and Verheyden, Synthesis and Antiviral Activity of Various Esters of 9–[(1,3–Dihydroxy–2–Propoxy)methyl]guanine, J. Pharmaceutical Sciences 76:180–184 (1987).

Welch, Larsson, Ericson, Oberg, Datema and Chattopadhyaya, The Chemical Synthesis and Antiviral Properties of an Acyclovir–Phospholipid Conjugate, Acta Chemica Scandinavica B 39:47–54 (1985).

Mayer, Hope and Cullis, Vesicles of Variable Sizes Produced by a Rapid Extrusion Procedure, Biochimica et Biophysica Acta 858:161–168 (1896).

Mayhew, Lazo, Vail, King and Green, Characterization of Liposomes Prepared Using a Microemulsifier, Biochimica et Biophysica Acta, 775:169–174 (1984).

Murthy and Agranoff, Stereospecific Synthesis and Enzyme Studies of CDP–Diacylglycerols, Biochimica et Biophysica Acta 712:473–483 (1982).

Norley, Huang and Rouse, Targeting of Drug Loaded Immunoliposomes to Herpes Simplex Virus Infected Corneal Cells: An Effective Means of Inhibiting Virus Replication in Vitro, J. Immunology 136:681–685 (1986).

Olson et al. (1979) Preparation of Liposomes of Defined Size Distribution by Extrusion Through Polycarbonate Membranes, Biochimica et Biophysica Acta 557:9–23.

Osto, Liposomes, Sci. Am. 256–103–111 (1987).

Poorthuis and Hostetler, Studies on Nucleotide Diphosphate Diacylglycerol Specificity of Acidic Phospholipid Biosynthesis in Rat Liver Subcellular Fractions, Biochimica et Biophysica Acta 431:408–415 (1976).

Poste, Kirsh, and Koestler, The Challenge of Liposome Targeting in Vivo, in Liposome Technology, vol. III. G. Gregoriadis, Ed., CRC Press, Boca Raton, pp. 1–28.

Prottey and Hawthorne, The Biosynthesis of Phosphatidic Acid and Phosphatidylinositol in Mammalian Pancreas, Biochem. J. 105:379–391 (1967).

Raetz and Kennedy, Function of Cytidine Diphosphate–Diglyceride and Deoxycytidine Diphosphate–Diglyceride in the Bio–Genesis of Membrane Lipids in Escherichia coli, J. Biological Chemistry 248:1098–1105 (1973).

Richman, Fischl, Grieco, Gottlieb, Volberding, Laskin, Leedom, Groopman, Mildvan, Hirsch, Jackson, Durack, Phil and Nusinoff–Lehrman, The Toxicity of Azidothymidine (AZT) in the Treatment of Patients with AIDS and AIDS–Related Complex, The New England Journal of Medicine 317:192–197 (1987).

Richman, Kornbluth and Carson, Failure of Dideoxynucleosides to Inhibit Human Immunodeficiency Virus Replication in Cultured Human Macrophages, J. Experimental Medicine 166:1144–1149 (1987).

Rittenhouse, Seguin, Fisher and Agranoff, Properties of a CDP–Diglyceride Hydrolase from Guinea Pig Brain, J. Neurochemistry 36:991–999 (1981).

Rosenthal and Geyer, A Synthetic Inhibitor or Venom Lecithinase A, J. Biological Chemistry 235:2202–2206 (1960).

Salahuddin, Rose, Groopman, Markham and Gallo, Human T Lymphotropic Virus Type III Infection of Human Alveolar Macrophages, Blood 68:281 (1986).

Scherphof, Liposomes in Biology and Medicine (a biased review) in Lipids and Biomembranes, Past. Present and Future, op den Kamp, J., Roelofsen, B. and Wirtz, K.W.Al, Eds., Elsevier North Holland, Amsterdam, pp. 113–136, (1986).

Shuto, Ueda, Itoh, Endo, Kukukawa, Imamura, Tsujino, Matsuda and Ueda, Synthesis of 5'–Phosphatidylnucleosides by Phospholipase Dcatalyzed Transphosphatidylation, Nucleic Acids Research Symposium Series No. 17, pp. 73–76 (1986).

Szoka and Papahadjopoulos (1978) Procedure for Preparation of Liposomes With Large Internal Aqueous Space and High Capture by Reverse–Phase Evaporation, Proc. Natl. Acad. Sci. USA 75:4194–1498.

Ter Schegget, Bosch, Van Baak, Hostetler and Borst, The Synthesis and Utilization of dCDP–Diglyceride By A Mitochondrial fraction From Rat Liver, Biochimica et Biophysica Acta 239:234–242 (1971).

Toorchen and Topai, Mechanisms of Chemical Mutagenesis and Carcinogenesis: Effects on DNA Replication of Methylation at the O6–Guanine Position of dGTP, Carcinogenesis 4:1591–1597 (1983).

Turcotte, Srivastava, Meresak, Rizkalla, Louzon and Wunz, I. Chemical Synthesis of CDP–Diacylglycerol Analogs Containing the Cytosine Arabinoside Moiety, Biochimica et Biophysica Acta 619:604–618 (1980).

Turcotte, Srivastava, Steim, Calabresi, Tibbetts and Chu, Cytotoxic Liponucleotide Analogs, Biochimica et Biophysica Acta 619:619–631 (1980).

METHODS OF TREATING VIRAL INFECTIONS USING ANTIVIRAL LIPONUCLEOTIDES

RELATED APPLICATION

This application is a continuation of U.S. Ser. No. 08/483,148, filed Jun. 7, 1995, now abandoned, which is a divisional of U.S. Ser. No. 08/415,769, filed Apr. 3, 1995, now U.S. Pat. No. 6,448,392, which is a continuation of U.S. Ser. No. 08/040,499, filed Mar. 31, 1993, now abandoned, which is a continuation of U.S. Ser. No. 07/373,088, filed Jun. 28, 1989, now U.S. Pat. No. 5,223,263, which is a continuation-in-part of U.S. Ser. No. 07/319,485, filed Mar. 6, 1989, now abandoned, which is a continuation-in-part of U.S. Ser. No. 07/216,412, filed Jul. 7, 1988, now abandoned.

BACKGROUND OF THE INVENTION

The present invention relates generally to the treatment of viral infections using lipid derivatives of antiviral nucleoside analogues. More particularly, the present invention relates to lipid, and especially phospholipid, derivatives of modified antiviral nucleoside analogues which can be integrated into the structure of liposomes, thereby forming a more stable liposomal complex which can deliver greater amounts of drugs to target cells with less toxicity.

The publications and other reference materials referred to herein are hereby incorporated by reference, and are listed for convenience in the bibliography appended at the end of this specification.

There has been a great deal of interest in recent years in the use of nucleoside analogues to treat viral infections. A nucleoside consists of a pyrimidine or purine base which is linked to ribose, a five-carbon sugar having a cyclic structure. The antiviral nucleoside analogues closely resemble natural nucleosides and are designed to inhibit viral functions by preventing the synthesis of new DNA or RNA. Nucleosides are enzymatically assembled into DNA or RNA.

During DNA synthesis, free nucleoside triphosphates (nucleosides with three phosphate groups attached) react with the end of a growing DNA chain. The reaction involves the linking of the phosphate group at the 5' position on the incoming nucleoside triphosphate with the hydroxyl group at the 3' position of the sugar ring on the end of the forming DNA chain. The other two phosphate groups are freed during the reaction, thereby resulting in the addition of a nucleotide to the DNA chain.

Nucleoside analogues are compounds which mimic the naturally occurring nucleosides sufficiently so that they are able to participate in viral DNA synthesis. However, the antiviral nucleoside analogues have strategically located differences in chemical structure which inhibit viral enzymes such as reverse transcriptase or which prevent further DNA synthesis once the analogue has been attached to the growing DNA chain.

Dideoxynucleosides are antiviral compounds that lack the hydroxyl groups normally present at the second and third position of ribose. When a dideoxynucleoside is incorporated into a growing DNA chain, the absence of the 3-OH group on its ribose group makes it impossible to attach another nucleotide and the chain is terminated. Dideoxynucleosides are particularly useful in treating retroviral infections where viral replication requires the transcription of viral RNA into DNA by viral reverse transcriptase. Other nucleoside analogues include deoxynucleosides and nucleosides analogues having only a fragment of ribose or other pentose connected to the base molecule.

Acquired immunodeficiency syndrome (AIDS) is caused by the human immunodeficiency virus (HIV). HIV infects cells bearing the CD4 (T4) surface antigen, such as CD4+ helper lymphocytes, CD4+ monocytes and macrophages and certain other CD4+ cell types. The HIV infection of CD4+ lymphocytes results in cytolysis and cell death which contributes to the immunodeficiency of AIDS; however, CD4+ monocytes and macrophages may not be greatly harmed by the virus. Viral replication in these cells appears to be more prolonged and less cytotoxic than in lymphocytes, and as a result, monocytes and macrophages represent important reservoirs of HIV infection. It has recently been discovered that macrophages may serve as reservoirs of HIV infection even in certain AIDS patients who test negative for the presence of HIV antibodies. No effective cure is available for AIDS, although dideoxynucleosides have been shown to prolong life and to reduce the incidence of certain fatal infections associated with AIDS.

Certain monocyte-derived macrophages, when infected with some strains of HIV, have been found to be resistant to treatment with dideoxycytidine, azidothymidine, and other dideoxynucleosides in vitro as shown by Richman, et al. (1). The resistance may be due in part to the low levels of dideoxynucleoside kinase which result in a reduced ability to phosphorylate AZT, ddC or ddA. Clearly, it would be useful to have more effective ways of delivering large amounts of effective antiviral compounds to macrophages infected with HIV or other viruses and other cells having viral infections. It would also be useful to have more effective ways of delivering antiviral compounds which not only increase their potency but prolong their efficacy.

Dideoxynucleoside analogues such as AZT are the most potent agents currently known for treating AIDS, but in a recent human trial, serious toxicity was noted, evidenced by anemia (24%) and granulocytopenia (16%) (2,3). It is desirable, therefore, to provide a means for administering AZT and other dideoxynucleosides in a manner such that the toxic side effects of these drugs are reduced. Further, it is desirable to provide selective targeting of the dideoxynucleoside to monocyte/macrophages to enhance the efficiency of the drug against viral infection in this group of cells. One way to do this is to take advantage of the uptake of liposomes by macrophages.

In 1965, Alex Bangham and coworkers discovered that dried films of phosphatidylcholine spontaneously formed closed bimolecular leaflet vesicles upon hydration (4). Eventually, these structures came to be known as liposomes.

A number of uses for liposomes have been proposed in medicine. Some of these uses are as carriers to deliver therapeutic agents to target organs. The agents are encapsulated during the process of liposome formation and released in vivo when liposomes fuse with the lipids of cell surface membrane. Liposomes provide a means of delivering higher concentrations of therapeutic agents to target organs. Further, since liposomal delivery focuses therapy at the site of liposome uptake, it reduces toxic side effects.

For example, liposomal antimonial drugs are several hundred-fold more effective than the free drug in treating leishmaniasis as shown independently by Black and Watson (5) and Alving, et al. (6). Liposome-entrapped amphotericin B appears to be more effective than the free drug in treating immunosuppressed patients with systemic fungal disease (7). Other uses for liposome encapsulation include restriction of doxorubicin toxicity (8) and diminution of aminoglycoside toxicity (9).

As previously mentioned, it is now thought that macrophages are an important reservoir of HIV infection (10, 11). Macrophages are also a primary site of liposome uptake (12, 13). Accordingly, it would be desirable to utilize liposomes to enhance the effectiveness of antiviral nucleoside analogues in treating AIDS and other viral infections.

The use of liposomes to deliver phosphorylated dideoxynucleoside to AIDS infected cells which have become resistant to therapy has been proposed in order to bypass the low dideoxynucleoside kinase levels.

Attempts have also been made to incorporate nucleoside analogues, such as iododeoxyuridine (IUDR), acylovir (ACV) and ribavirin into liposomes for treating diseases other than AIDS. However, these attempts have not been entirely satisfactory because these relatively small water soluble nucleoside analogues tend to leak out of the liposome rapidly (14, 15), resulting in decreased targeting effectiveness. Other disadvantages include the tendency to leak out of liposomes in the presence of serum, difficulties in liposome formulation and stability, low degree of liposomal loading, and hydrolysis of liposomal dideoxynucleoside phosphates when exposed to acid hydrolases after cellular uptake of the liposomes.

Attempts have also been made to combine nucleoside analogues, such as arabinofuranosylcytosine (ara-C) and arabinofuranosyladenine (ara-A), with phospholipids in order to enhance their catabolic stability as chemotherapeutic agents in the treatment of various types of cancer (16). The resulting agents showed a decreased toxicity and increased stability over the unincorporated nucleoside analogues. However, the resulting agents exhibited poor cellular uptake (16) and poor drug absorption (17).

In order to use nucleoside analogues incorporated into liposomes for treating viral infections more effectively, it is desirable to increase the stability of the association between the liposome and the nucleoside analogue.

In order to further enhance the effectiveness of these antiviral liposomes, it would be desirable to target the liposomes to infected cells or sites of infection. Greater specificity in liposomal delivery may be obtained by incorporating monoclonal antibodies or other ligands into the liposomes. Such ligands will target the liposomes to sites of liposome uptake capable of binding the ligands. Two different approaches for incorporating antibodies into liposomes to create immunoliposomes have been described: that of Huang and coworkers (18) involving the synthesis of palmitoyl antibody, and that of Leserman, et al. (19) involving the linkage of thiolated antibody to liposome-incorporated phosphatidylethanolamine (PE).

The methods disclosed here apply not only to dideoxynucleosides used in the treatment of AIDS and other retroviral diseases, but also to the use of antiviral nucleosides in the treatment of diseases caused by other viruses, such as herpes simplex virus (HSV), human herpes virus 6, cytomegalovirus (CMV), hepatitis B virus, Epstein-Barr virus (EBV), and varicella zoster virus (VZV). Thus, the term "nucleoside analogues" is used herein to refer to compounds that can inhibit viral replication at various steps, including inhibition of viral reverse transcriptase or which can be incorporated into viral DNA or RNA, where they exhibit a chain-terminating function.

SUMMARY OF THE INVENTION

The invention provides a composition for use in treating viral infections, including HIV (AIDS), herpes simplex virus (HSV), human herpes virus 6, cytomegalovirus (CMV), hepatitis B virus, Epstein-Barr virus (EBV), and varicella zoster virus (VZV). The composition may contain, in addition to a pharmaceutically acceptable carrier, a lipophilic antiviral agent prepared by chemically linking an antiviral nucleoside analogue to at least one lipid species. The antiviral nucleoside analogue may be linked to the lipid through a monophosphate, diphosphate or triphosphate group. The invention, further, provides a method for incorporating such lipid derivatives of antiviral agents into liposomes for improved delivery of the antiviral agent. A liposome comprises a relatively spherical bilayer which is comprised wholly or in part of the above-described lipid derivatives of antiviral agents. The liposome may also contain pharmacologically inactive lipids. Further, the liposome may contain a ligand, such as a monoclonal antibody to a viral binding site (such as $CD_4$), or other binding protein. Such a ligand provides additional specificity in the delivery site of the antiviral agent. The invention provides a method for incorporating such ligands into antiviral liposomes.

In one preferred embodiment, the compound is a phosphatidyldideoxynucleoside or a dideoxynucleoside diphosphate diglyceride. In another, the lipid species may comprise at least one acyl ester, ether, or vinyl ether group of glycerol-phosphate. Phosphatidic acids having at least one acyl ester, ether, or vinyl ether group may also serve as a favored lipid species.

In another embodiment, the nucleoside analogue is a purine or pyrimidine linked through a β-N-glycosyl bond to a pentose residue that lacks at least one of the 2' or 3' carbons, but retains the 5' carbon, and the phosphate group is bound to the 5' carbon (i.e., what would have been the 5' carbon in a complete pentose moiety). In another embodiment of the invention, the lipid species is an N-acyl sphingosine.

In some preferred embodiments, the acyl or alkyl groups of the lipid species, of whatever linkage, as for example ester, ether or vinyl ether, comprise 2 to 24 carbon atoms. In one variation, at least one of the acyl or alkyl groups is saturated. In another, at least one of the acyl or alkyl groups has up to six double bonds. In yet another embodiment, an acyl or alkyl group may be attached directly by ester or alkyl linkage to the 5'-hydroxyl of the nucleoside.

In still another, the lipid moiety is a glyceride and the glyceride has two acyl groups that are the same or different. In still another embodiment of the invention, the lipid species is a fatty alcohol residue which is joined to a phosphate linking group through an ester bond. The compound may advantageously have from one to three phosphate groups, and at least one fatty alcohol ester, and may have two or more fatty alcohol residues that are the same or different in structure. These fatty alcohols are preferably linked to the terminal phosphate group of the compound.

Moreover, the invention includes a composition wherein, in addition to the compound, the liposome further comprises phospholipids selected from the group consisting of phosphatidylcholine, phosphatidylethanolamine, phosphatidylglycerol, phosphatidylserine, phosphatidylinositol and sphingomyelin.

In one embodiment of the invention, the percentage of antiviral agent is 0.01 to 100 percent by weight of the liposome.

In another embodiment, the liposome further comprises a ligand bound to a lipid substrate. The ligand may be an antibody, such as a monoclonal antibody to a viral antigen. The viral antigen could be gp41 or gp110 of HIV, or could be any other suitable viral antigen. In one embodiment, the ligand is CD4 receptor protein, or CD4 protein itself. Alternatively, the ligand is an antibody to CD4 or a protein or other substance that binds CD4.

The invention also contemplates a composition for use in treating viral and retroviral infections, comprising a liposome formed at least in part of an lipophilic antiviral agent, the agent comprising a nucleoside analogue having a base and a pentose residue with at least one lipid species attached to the nucleoside analogue through a monophosphate, diphosphate or triphosphate linking group at the 5' hydroxyl of the pentose residue of the nucleoside analogue, and a pharmaceutically acceptable carrier therefore.

Thus, there is provided a composition having antiviral properties, comprising an antiviral nucleoside analogue having a base portion comprising a substituted or unsubstituted purine or pyrimidine, and a sugar portion comprising a pentose residue, and a lipid moiety linked to the pentose residue, with the proviso that the composition is in the form of a liposome when the pentose residue is ribose and the base portion is cytosine, and when the pentose residue is arabinofuranose and the base portion is cytosine or adenine. In one embodiment, the nucleoside analogue is a nitrogenous base which is a purine, pyrimidine, or a derivative thereof, and the pentose residue is a 2',3'-dideoxy, 2',3'-didehydro, azido or halo derivative of ribose, or an acyclic hydroxylated fragment of ribose. The pentose residue may thus be a 2',3'-dideoxyribose, and the nucleoside analogue may be 2',3'-dideoxycytidine, 2',3'-dideoxythymidine, 2',3'-dideoxyguanosine, 2',3'-dideoxyadenosine, 2',3'-dideoxyinosine, or 2,6 diaminopurine, 2',3'-dideoxyriboside.

In another embodiment, the pentose residue is a 2',3'-didehydroribose and the nucleoside is 2',3'-didehydrothymidine, 2',3'-didehydrocytidine carbocyclic, or 2',3'-didehydroguanosine. In still another embodiment, the pentose residue is an azide derivative of ribose, and the nucleoside is 3'-azido-3'-deoxythymidine, 3'-azido-3'-deoxyguanosine, or 2,6-diaminopurine-3-azido-2',3'dideoxyriboside.

In still another embodiment of the invention, the pentose residue is a halo derivative of ribose and the nucleoside is 3'-fluoro-3'-deoxythymidine, 3'-fluoro-2',3'-dideoxyguanosine, 2',3'-dideoxy-2'-fluoro-ara-adenosine, or 2,6-diaminopurine-3'-fluoro-2',3'-dideoxyriboside. The invention also includes halo derivatives of the purine or pyrimidine rings, such as, for example, 2-chloro-deoxyadenosine. Alternatively, the pentose residue is an acyclic hydroxylated fragment of ribose, and the nucleoside is 9-(4,-hydroxy-1',2'-butadienyl) adenine, 3-(4,-hydroxy-1', 2'-butadienyl) cytosine, 9-(2-phosphonylmethoxyethyl) adenine or phosphonomethoxydiaminopurine.

In accordance with another aspect of the invention, the nucleoside analogue is acyclovir, gancyclovir, 1-(2'-deoxy-2'-fluoro-1-β-D-arabinofuranosyl)-5-iodocytosine (FIAC) or 1(2'-deoxy-2'-fluoro-1-β-D-arabinofuranosyl)-5-iodouracil (FIAU).

In all of the foregoing compositions, a monophosphate, diphosphate, or triphosphate linking group may be provided between the 5' position of the pentose residue and the lipid species. Alternatively, there may be an aliphatic bridge comprising two functional groups and having from 0 to 10 carbon atoms between the functional groups, the bridge joining the lipid and the pentose residue. In still further embodiments of the invention, the lipid species is a fatty acid, a monoacylglycerol, a diacylglycerol, or a phospholipid. The phospholipid may have a head group comprising a sugar or a polyhydric alcohol. Specific examples of phospholipids include bis(diacylglycero)-phosphate and diphosphatidylglycerol. Other examples of lipid species include D,L-2,3-diacyloxypropyl-(dimethyl)-beta-hydroxyethyl ammonium groups.

In accordance with another aspect of the present invention, the lipid species comprises from 1 to 4 fatty acid moieties, each the moiety comprising from 2 to 24 carbon atoms. Advantageously, at least one fatty acid moiety of the lipid species is unsaturated, and has from 1 to 6 double bonds.

Particular examples of these compositions include 3-phosphonomethoxyethyl-2,6-diaminopurine; 1,2-diacylglycerophospho-5'-(2',3'-dideoxy)thymidine.

Specific compositions are provided having the formula:

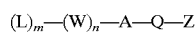

wherein

Z is the base portion of the nucleoside analogue, Q is the pentose residue, A is O, C, or S, W is phosphate, n=0 to 3, and L is a lipid moiety wherein m=1 to 5, and wherein each L is linked directly to a W except when n=0, in which case each L is linked directly to A.

Also included are compositions having the formula:

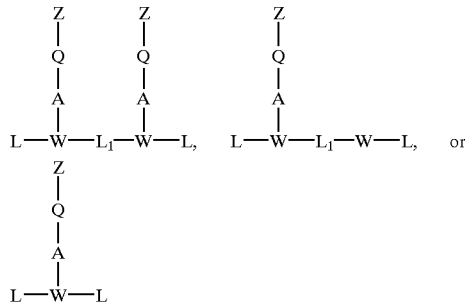

wherein Z is the substituted or unsubstituted purine or pyrimidine group of the nucleoside analogue, Q is the pentose residue, W is phosphate, A is O, C, or S, $L_1$ is ($CH_2$—CHOH—$CH_2$), and L is a lipid moiety.

In one embodiment of the invention, with reference to the foregoing formulas, each L is independently selected from the group consisting of R,

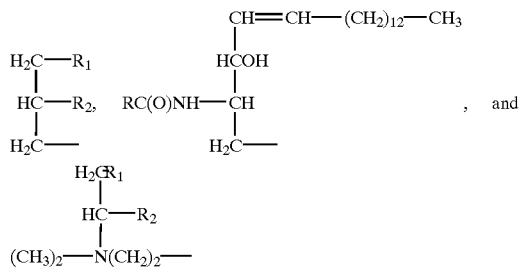

wherein R, $R_1$ and $R_2$ are independently $C_2$ to $C_{24}$ aliphatic groups and wherein R, $R_1$ and $R_2$ independently have from 0 to 6 sites of unsaturation, and have the structure $CH_3$—$(CH_2)_a$—(CH=CH—$CH_2)_b$—$(CH_2)_c$—Y wherein the sum of a and c is from 1 to 23, and b is 0 to 6, and wherein Y is C(O)O—, C—O—, C=C—O—, C(O)S—, C—S—, or C=C—S—.

In one embodiment of the foregoing compositions, the pentose residue comprises ribose, dideoxyribose, didehydroribose, or an azido or halosubstituted ribose, attached at the 9 position of the purine or at the 1 position of the pyrimidine.

The present invention also provides a method for synthesizing a lipid derivative of an antiviral nucleoside, comprising the step of reacting an antiviral nucleoside, having a ribose hydroxyl group, with a phospholipid in the presence of a coupling reagent whereby the nucleoside is joined to the phospholipid by a phosphate bond at the position of the ribose hydroxyl group. In one preferred embodiment, the phospholipid is a diacyl phosphate. In another, the phospholipid is a phosphatidic acid or a ceramide. Also provided herein is a method of synthesizing a lipid derivative of an antiviral nucleoside, comprising the steps of reacting an antiviral nucleoside monophosphate with a reagent HL, wherein L represents a leaving group, to form a nucleoside $PO_4$-L, reacting the nucleoside $PO_4$-L with a phosphatidic acid to bind the acid to the nucleoside through a pyrophosphate bond. In one variation of the method, the nucleoside monophosphate is AZT 5'-monophosphate.

Still a further method provided by the present invention is a method of synthesizing a glyceride derivative of a nucleoside analogue, comprising the step of joining a monoglyceride or diglyceride and an antiviral nucleoside monophosphate with a coupling agent in the presence of a basic catalyst. In one embodiment, the glyceride is 1-O-stearoylglycerol and the nucleoside is AZT monophosphate.

Also a part of the present invention is a method for preparing a suspension of liposomes for use in treating viral and retroviral infections in a mammal, comprising providing a lipophilic antiviral agent comprising at least one lipid species attached to a nucleoside analogue through a monophosphate, diphosphate or triphosphate linking group at the 5' position of the pentose residue of the nucleoside, combining the lipophilic antiviral agent and a pharmacologically acceptable aqueous solvent to form a mixture, and forming liposomes from the lipophilic antiviral agent. The liposomes may be formed, for example, by sonication, extrusion or microfluidization. In one preferred embodiment, the combining step further comprises including in the combination a pharmacologically inactive lipophilic lipid. This inactive lipid can be, for example, a phosphatidylethanolamine, a sphingolipid, a sterol or a glycerophosphatide. The method also may include treating the liposomes with thio-antibodies to produce immunoliposomes, or including in the combination an lipophilic lipid which is, in part, comprised of a ligand. Thus, the liposome may include a ligand bound to a lipid substrate.

In addition, the invention includes a method for treating retroviral and viral infections in a mammal, such as a human, by administering a sufficient quantity of the antiviral nucleoside analogues described herein to deliver a therapeutic dose of the antiviral agent to the mammal. In a preferred embodiment, the method is used to treat retroviral and viral infections in a mammal, wherein the retrovirus has become resistant to therapy with conventional forms of an antiviral agent. The present invention also includes a method for treatment of patients having strains of HIV that have developed resistance to AZT or reduced sensitivity to AZT, comprising the step of administering a composition of the present invention to such patient in an effective, retrovirus-inhibiting dosage. Also included in the present invention is a method for treating a viral infection in a mammal, comprising the step of administering an effective amount of a composition as described herein to a mammal. The infection may be a herpes simplex infection, and the composition may be phosphatidylacyclovir. Alternatively, the virus may be HIV retrovirus, and the composition may be 5'-palmitoylAZT. The method includes use where the retrovirus is a strain of HIV that has developed resistance to a nucleoside analogue.

Also disclosed herein is a method for prolonging the antiviral effect of a nucleoside analogue in a mammal, comprising administering the nucleoside analogue to the mammal in the form of the nucleoside-lipid derivatives disclosed herein. Also disclosed is a method for avoiding or overcoming resistance of the retrovirus to nucleoside analogues through administering the analogue in the form of the lipid derivative compositions disclosed herein.

Finally, the present invention includes use of these compositions in the preparation of a medicament for treatment of a human viral infection.

Liposomal delivery of antiretroviral and antiviral drugs results in higher dosing of macrophage and monocyte cells which take up liposomes readily. The unique advantages of the present invention are that the lipid derivatives of the antiviral nucleosides are incorporated predominantly into the phospholipid layer of the liposome rather than in the aqueous compartment. This allows larger quantities of antiviral analogue to be incorporated in liposomes than is the case when water soluble phosphate esters of the nucleosides are used. Complete incorporation of the antiviral derivative into liposomes will be obtained, thus improving both the drug to lipid ratio and the efficiency of formulation. Further, there will be no leakage of the antiviral lipid analogues from the liposome during storage. Finally, liposomal therapy using these compositions allows larger amounts of antiviral compound to be delivered to the infected macrophage and monocyte cells. Therapy with liposomal compositions containing site specific ligands allows still greater amounts of antiviral compounds to be delivered with increased specificity.

Another novel advantage of this invention is that each class of lipid derivatives of antiviral nucleosides disclosed below is believed to give rise directly to antiviral phosphorylated or non-phosphorylated nucleosides upon cellular metabolism.

A further advantage of this invention is that the novel lipid derivatives are incorporated into the cell, protecting the cell for prolonged periods of time, up to or exceeding 48 hours after the drug is removed.

These and other advantages and features of the present invention will become more fully apparent from the following description and appended claims.

DETAILED DESCRIPTION OF THE INVENTION

Figure 1:
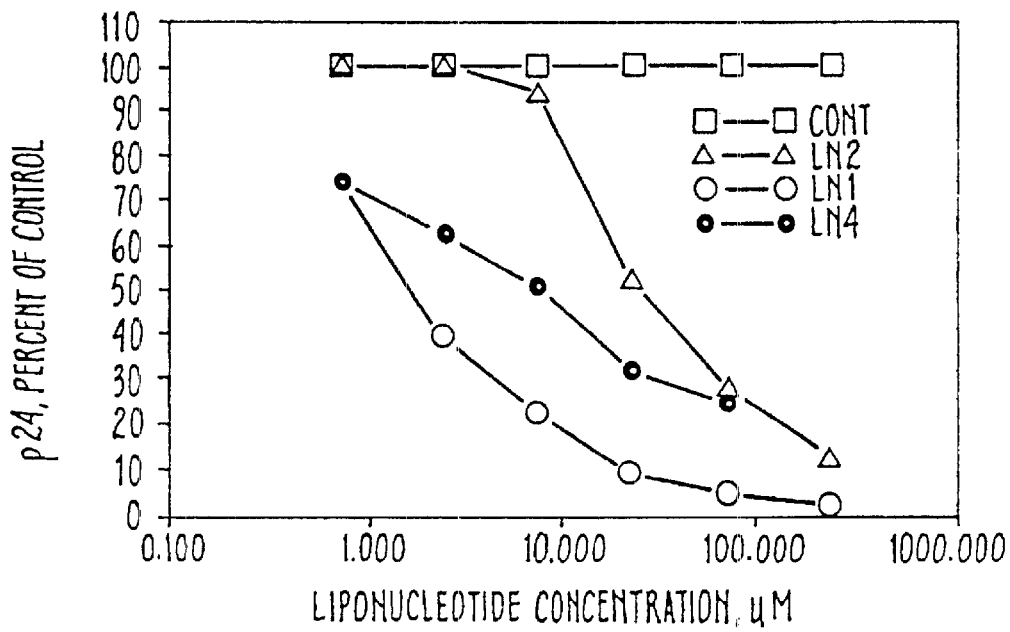
FIGS. 1–5 are graphs plotting p24 production by HIV-infected cells as a function of the amount of the composition of the present invention administered in vitro.

The present invention involves lipid derivatives of nucleoside analogues which can be incorporated into the lipid bilayer of liposomes. These derivatives are converted into nucleoside analogues by constituent cellular metabolic processes, and have antiviral effects in vivo and in vitro.

Suitable lipid derivatives of nucleoside analogues comprise phosphatidyl nucleosides, nucleoside diphosphate diacylglycerols, nucleoside acyl phosphates, and ceramide phosphonucleosides. With the exception of the acyl phosphates, which can include from one to five acyl groups, the lipid derivatives of these compositions provide one or two hydrophobic acyl groups to anchor the nucleoside in the lipid bilayer of the liposome. The present invention also comprises lipid derivatives capable of providing additional acyl groups, and hence greater anchoring strength for nucleoside analogues. The increase in anchoring strength makes it possible to utilize nucleoside analogues of greater polarity in liposome formulations. Accordingly we disclose additional nucleoside structures of this type for use in liposomal therapies. We also disclose lipid derivatives of nucleoside analogues in which the lipid group is directly attached to the nucleoside, rather than through a phosphate link.

Nomenclature

The lipid derivatives of the present invention are made up of complex structures which can only be rigorously defined by cumbersome terminology. For purposes of clarity, the descriptions of lipid and nucleosides components and their combinations will be in terms of commonly used trivial names, familiar to those in the art. For example, the well known drug, 3'-azido-3'-deoxythymidine, will be frequently referred to as AZT. Similarly the derivative of AZT comprising a 1,2 diacylglycerol-3-phosphate moiety, will be frequently referred to as phosphatidylAZT or PAZT. Parallel derivatives of dideoxythymidine or dideoxycytidine will correspondingly be referred to as phosphatidylddT or pddT and phosphatidylddC and pddC. Derivatives of halogenated nucleosides will be referred to as, for example, phosphatidyl-3'BrddT.

The nucleoside analogues of the invention can be any nucleoside that does not occur naturally in the species to be treated for viral infection. It may comprise a naturally occurring purine or pyrimidine base attached to an analogue of a naturally occurring ribose group. It may likewise comprise an analogue of a purine or pyrimidine base attached to a ribose or deoxyribose group which is present in naturally occurring nucleosides. Alternatively, both the base and the ribose moieties of the nucleoside analogues may be analogues of those found in nature. A nucleoside analogue may also comprise either a normal base or a base analogue attached to a non-ribose sugar moiety.

Analogues of both the purine or pyrimidine base and the ribose group can differ from a corresponding naturally occurring moiety by having new substituent groups attached thereto, by having naturally occurring substituent groups deleted therefrom, or by having atoms normally present replaced by others. Examples of analogues formed by substitution are 2,6-diaminopurine and 3'-azido-3'deoxyribose; by deletion, 6-oxypurine or didehydroribose; by replacement, 8-azaguanine.

Nucleoside analogues may also comprise a purine or pyrimidine base attached to the pentose moiety in a non-naturally occurring linkage, such as, for example through the nitrogen at the 3 position rather than the 1 position of the pyrimidines.

In general, the nucleoside analogues used in preparing the liposomes of the present invention will have a purine or pyrimidine base, e.g., adenine, guanine, cytosine or thymine, or an analogue thereof, attached to a pentose, such as ribose or a ribose residue and/or derivative. The attachment is through the nitrogen in the 9 position of the purines and through the nitrogen in the 1 position of the pyrimidines. These nitrogens are linked by a β-N-glycosyl linkage to carbon 1 of the pentose residue.

The pentose residue may be a complete pentose, or a derivative such as a deoxy- or dideoxypentose. In addition, the pentose residue can be a fragment of a pentose, such as a hydroxylated 2-propoxymethyl residue or a hydroxylated ethoxymethyl residue. Particular nucleoside residues having these structures include acyclovir and gancyclovir. The pentose may also have an oxygen or sulfur substitution for a carbon atom at, for example, the 3'position of deoxyribose (BCH-189).

The phosphate groups are generally connected to the 5' carbon of the pentoses in the compounds of the present invention; however, compounds wherein the phosphate groups are attached to the 3' hydroxyl group of the pentose are within the invention if they possess antiviral activity. Where lipids are linked directly to pentose groups, those linkages may also be made either through the 3' or preferably through the 5' pentose carbon.

It is important to recognize that in compounds having pentose residues that are not complete pentoses, the phosphate groups are connected to the carbon that would have been the 5' carbon if the pentose were complete. In these pentose fragments, the 2' and/or 3' carbons may be missing; nevertheless, they are considered to be nucleoside derivatives within the meaning of present invention, and the carbon atom to which the phosphate groups are connected will generally be referred to herein as the 5' carbon for purposes of consistency of usage.

Any lipid derivative of a nucleoside analogue having an antiviral activity is within the scope of the invention. The antiviral activity may reside in any component of the lipid-nucleoside complex, that is, in a nucleoside base analogue, in a ribose analogue, or in the substitution of another pentose for ribose. It may also reside in the complex as a whole, wherein, for example, a weakly antiviral analogue or one possessing imperceptible or latent viral activity becomes more potent following its incorporation into a lipid derivative of a nucleotide.

Nucleosides known to have such activity are members of the class comprising 3'-azido-2',3'-dideoxypyrimidine nucleosides, for example, AZT, AZT-P-AZT, AZT-P-ddA, AZT-P-ddI, AzddClU, AzddMeC, AzddMeC N4-OH, AzddMeC N4Me, AZT-P-CyE-ddA, AzddEtU(CS-85), AzddU (CS-87), AzddC(CS-91), AzddFC, AzddBrU, and AzddIU; the class comprising 3'-halopyrimidine dideoxynucleosides, for example, 3-FddClU, 3-FddU, 3-FddT, 3-FddBrU, and 3-FddEtU; the class comprising 2',3'-didehydro-2',3'-dideoxynucleosides (D4 nucleosides), for example, D4T, D4C, D4MeC, and D4A; the class comprising 2',3'-unsubstituted dideoxypyrimidine nucleosides, for example, 5-F-ddC, ddC and ddT; the class comprising 2',3'-unsubstituted dideoxypurines nucleosides, for example, ddA, ddDAPR(diaminopurine), ddG, ddI, and ddMeA(N6 methyl); and the class comprising sugar-substituted dideoxypurine nucleosides, for example, 3-$N_3$ddDAPR, 3-$N_3$ddG, 3-FddDAPR, 3-FddG, 3-FddaraA, and 3-FddA, wherein Me is methyl, Et is ethyl and CyEt is cyanoethyl.

Other suitable nucleotide analogues may be antiviral agents like acyclovir or gancyclovir (DHPG), or other analogues, as described below. Preferred dideoxy derivatives are those used in the treatment of AIDS, including 3'-azido-3'-deoxythymidine (azidothymidine or AZT); 2',3'-dideoxythymidine (ddT); 2',3'-dideoxycytidine (ddC); 2',3'-dideoxyadenosine (ddA); and 2',3'-dideoxyguanosine (ddG). AZT, ddT, and ddC are most preferred analogues at present. The didehydropyrimidines, as well as carbovir, a carbocyclic 2',3'-didehydroguanosine, are also preferred. The 3'-azido derivatives of deoxyguanosine (AZG) and the pyrimidine, deoxyuridine, and the 3'-fluoro derivatives of deoxythymidine and deoxyguanosine are preferred as well. Among the 2',6'-diaminopurines, the 2',3'-deoxyriboside and its 3'-fluoro and 3'-azido derivatives are preferred. Also preferred is 2-chloro-deoxyadenosine.

Among the acyclic sugar derivatives, 9-(4,-hydroxy-1',2'-butadienyl)adenine (adenallene) and its cytosine equivalent are preferred. Preferred acyclic derivatives having a purine or diaminopurine base are 9-(2-phosphonylmethoxyethyl) adenine and phosphonomethoxyethyl deoxydiaminopurine (PMEDADP).

Stereoisomers of these nucleosides, such as 2'-fluoro-ara-ddA, may be advantageous because of their resistance to acid-catalyzed hydrolysis of the glycosidic bond, which prolongs their antiviral activity. In such cases, they are preferred.

For treating herpes, cytomegalovirus and hepatitis B infections, one may utilize the lipid derivatives of acyclovir, gancyclovir, 1-(2'-deoxy-2'-fluoro-1-β-D-arabinofuranosyl)-5-iodocytosine (FIAC) or 1(2'-deoxy-2'-fluoro-1-β-D-arabinofuranosyl)-5-iodouracil (FIAU).

The lipids are preferably attached to the nucleoside analogues through phosphate linkages. Lipid derivatives comprising a phosphate link between a nucleoside analogue and lipid may be prepared from phospholipids, phosphorylated nucleoside analogs, or both. Suitable phospholipids comprise phosphoglycerides, sphingolipids, or acyl phosphates.

Lipid derivatives of nucleoside analogue in which lipids are linked either through mono-, di-, or triphosphate groups may be prepared from phosphorylated nucleoside analogues. Phosphorylated nucleoside analogues are known. The dideoxynucleoside analogue is phosphorylated according to conventional procedures such as the phosphorous oxychloride method of Toorchen and Topal (20). The preferred modified analogue is the 5'-monophosphate. Since AZT, ddC and other dideoxynucleosides have only the 5'-hydroxyl, only the 5'-monophosphate is formed during phosphorylation; however, in other analogues in which the 3'hydroxyl is present, a 3'-monophosphate can be formed. The diphosphate and triphosphate analogues of antiviral nucleosides may also be used.

The aliphatic groups of the lipid moieties preferably have chain lengths of two to twenty-four carbon atoms and have zero to six double bonds. The aliphatic groups may be attached to the glycerol moiety by acyl, ether or vinyl ether bonds.

Synthetic Methods

The lipid-nucleotide compounds of the present invention can be synthesized according to general methods applicable to all lipids and all antiviral nucleosides described below, as indicated in the flow diagram of Figure and demonstrated specifically in Examples 1 through 7.

Lipids comprising fatty acids, alcohols, glycerides and phospholipids may be purchased from commercial suppliers (Avanti Polar Lipids, Inc., Pelham, Ala. 35124) or may be synthesized according to known methods. Antiviral nucleoside analogues are available from Aldrich, Milwaukee, Wis. or from Sigma, St. Louis, Mo.

It is important that all traces of water be removed from the reactants in order for the coupling reactions to proceed. Therefore, the lipids are first either freeze-dried by solvent evaporation under vacuum, or in a vacuum oven over $P_2O_5$. The reactions are also carried out under an inert gas, such as, for example, argon.

The compounds of the invention can be formed according to synthetic procedures which couple a phospholipid to a nucleoside analogue or which couple a phospholipid to a nucleoside analogue monophosphate or diphosphate, wherein the phosphate group is located on the ribose group of the nucleoside, at either the 3' or preferably the 5' location.

Lipids suitable for coupling to nucleosides, comprising primarily long chain fatty acids or alcohols, monoglycerides or diglycerides, ceramides and other lipid species described below, may be phosphorylated by treatment with appropriate agents, for example using phenyl phosphorodichloridate according to the procedure of Brown (32), by treatment with phosphorus oxychloride as in Example 6, or by other known phosphorylation procedures.

In the first type of synthesis, a phospholipid, such as, for example, a phosphatidic acid, is coupled to a selected nucleoside analogue at either the 3' or 5' hydroxyl by means of a coupling agent, such as, for example, 2,4,6-triisopropylbenzenesulfonyl chloride in the presence of a basic catalyst, for example, anhydrous pyridine, at room temperature. Other coupling agents, such as dicyclohexylcarbodiimide can be used.

Lipid derivatives may also be synthesized by coupling a phosphatidic acid to an antiviral nucleoside monophosphate through a pyrophosphate bond. In this procedure, the nucleoside monophosphate or diphosphate is converted to a derivative having a leaving group, for example, morpholine, attached to the terminal phosphate group, according to the procedure of Agranoff and Suomi (21) and as illustrated in Example 4, for preparing a derivative of AZT and Example 6, for a derivative of ddA. A coupling of the phosphatidic acid and the nucleoside phosphate morpholidate occurs on treatment of a dry mixture of the two reactants with a basic catalyst, such as anhydrous pyridine, at room temperature.

The reactions are followed using thin layer chromatography (TLC) and appropriate solvents. When the reaction, as determined by TLC is complete, the product is extracted with an organic solvent and purified by chromatography on a support suitable for lipid separation, for example, silicic acid.

The synthesis of products comprising adenine or cytidine having reactive amino groups may be facilitated by blocking those groups with acetate before the coupling reaction by treatment with acetic anhydride; after the chromatography of the final product, the amino groups are unblocked using ammonium hydroxide (Example 3).

Lipid Derivatives

Compounds which will be most effective will have a lipid portion sufficient to be able to incorporate the material in a stable way into a liposomal bilayer or other macromolecular array.

Some preferred lipid derivatives of nucleoside analogues that are within the scope of the present invention fall into four general classes:

1. Antiviral Phosphatidylnucleosides

The structure of these antiviral lipid compounds is shown below:

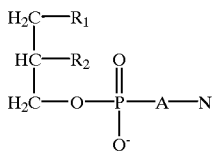

where N is a "chain terminating" dideoxynucleoside such as AZT, ddC, ddA, ddI, or another antiviral nucleoside such as acyclovir or gancyclovir, A is a chalcogen (O, C or S), and $R_1$ and $R_2$, which may be the same or different, are $C_1$ to $C_{24}$ aliphatic groups, having from 0 to 6 sites of unsaturation, and preferably having the structure $CH_3$—$(CH_2)_a$—$(CH=CH-CH_2)_b$—$(CH_2)_c$—Y wherein the sum of a and c is from 1 to 23; and b is 0 to 6; and wherein Y is C(O)O⁻, C—O⁻, C=C—O⁻, C(O)S—, C—S—, C=C—S—, forming acyl ester, ether or vinyl ether bonds, respectively, between the aliphatic groups and the glycerol moiety. These aliphatic groups in acyl ester linkage therefore comprise naturally occurring saturated fatty acids, such as lauric, myristic, palmitic, stearic, arachidic and lignoceric, and the naturally occurring unsaturated fatty acids palmitoleic, oleic, linoleic, linolenic and arachidonic. Preferred embodiments comprise a monoester or diester, or a 1-ether, 2-acyl ester phosphatidyl derivative. In other embodiments, the aliphatic groups can be branched chains of the same carbon number, and comprise primary or secondary alkanol or alkoxy groups, cyclopropane groups, and internal ether linkages.

This class of compounds may be prepared, for example, from the reaction of a diacylphosphatidic acid and an antiviral nucleoside analogue in pyridine as described for the preparation of 1,2 dimyristoylglycerophospho-5'-(3'-azido-3'-deoxy)thymidine in Example 1.

Upon liposomal uptake, the compounds are believed to undergo metabolism by the phospholipases present in the cell. For example, in the specific case of a diacylphosphatidyl derivative of a nucleoside, phospholipase C would act to give a diacylglycerol and the nucleoside monophosphate as shown below:

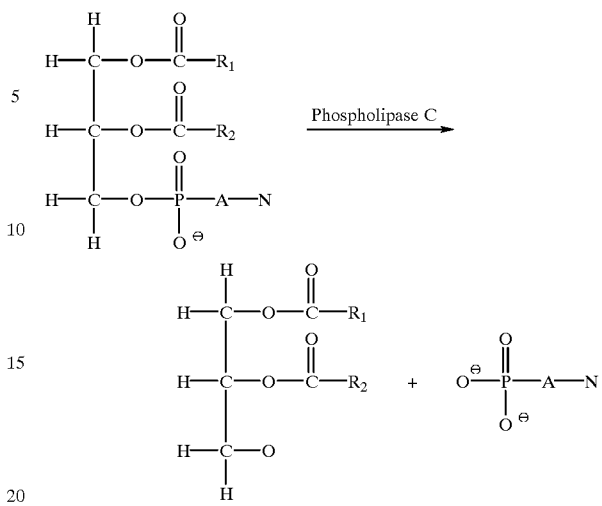

Alternatively, the same phosphatidylnucleoside may be hydrolyzed by phospholipase A and lysophospholipase followed by phosphodiesterase to give glycerol and nucleoside monophosphate by the sequence shown below:

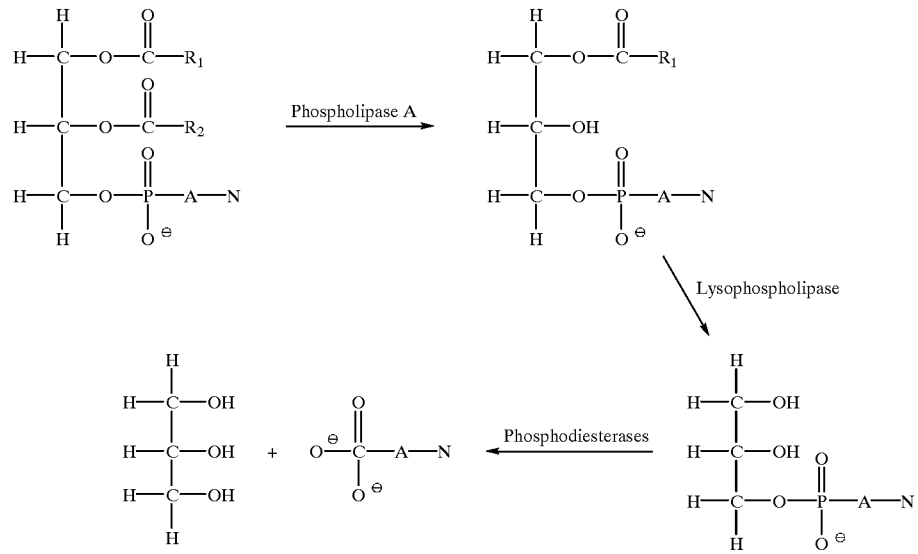

2. Antiviral Nucleoside Diphosphate Diglycerides

The chemical structure of this class of compounds is shown below:

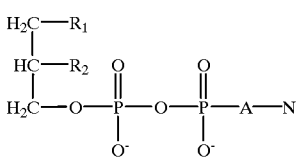

where N, A and $R_1$ and $R_2$ are as described above.

Nucleoside diphosphate diglycerides are known. The antiviral nucleoside diphosphate diglycerides may be prepared from phosphatidic acid and the antiviral nucleotide monophosphomorpholidates by the method of Agranoff and Suomi (21) as modified by Prottey and Hawthorne (22). This type of synthesis is presented in Example 4 for the synthesis of AZT 5'-diphosphate dipalmitoyl glycerol.

Upon liposomal delivery to cells, this class of compounds will take part in several types of reactions since it is an analogue of CDP-diglyceride, an important naturally-occurring intermediate in the biosynthesis of phosphatidylglycerol, cardiolipin and phosphatidylinositol as shown below:

and phosphatidic acid, providing a second manner in which the nucleoside monophosphate can be formed in the target cells.

3. Antiviral Nucleoside Acyl Phosphates

Another way to introduce a lipid compound into cells by means of liposomes is to synthesize acyl esters of the nucleoside monophosphates, diphosphates or triphosphates. This synthesis may be carried out according to the procedure

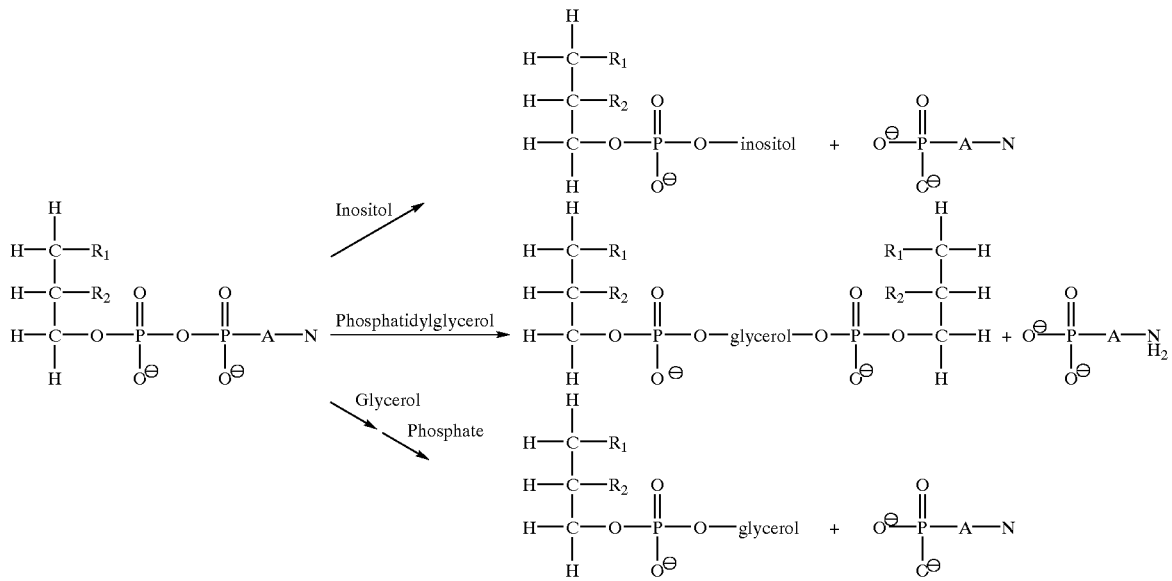

All of these reactions generate nucleoside monophosphate and a new phospholipid. It is important to note that Poorthuis and Hostetler (23) showed previously that a variety of nucleosides could substitute for CDP-diglyceride in these reactions, including UDP-diglyceride ADP-diglyceride and GDP-diglyceride (23). Significantly, Ter Scheggett, et al. (24) synthesized deoxy CDP-diglyceride and found that it could also replace CDP-diglyceride in the mitochondrial synthesis of phosphatidylglycerol and cardiolipin, thereby suggesting the possibility of using these novel compounds to generate the antiviral nucleoside phosphates in the target cells.

CDP-diglyceride hydrolase catalyzes another important metabolic conversion which gives rise to nucleoside monophosphate and phosphatidic acid, as shown below:

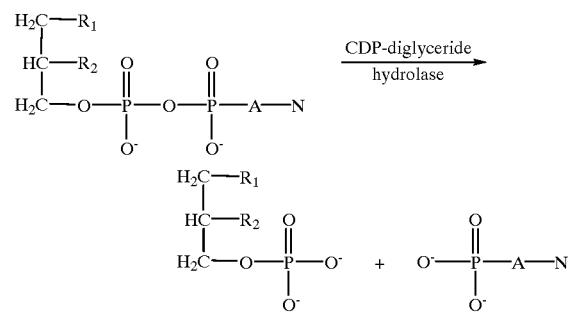

This pathway was first described in mammalian tissues by Rittenhouse, et al. (25). This enzyme, which is a pyrophosphatase, is expected to cleave dideoxynucleoside diphosphate diglyceride to the nucleoside monophosphate in Example 5 for the synthesis of dihexadecyl phospho-5'-dideoxycytidine.

The structure of a diacylphosphonucleoside is shown below:

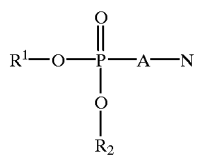

wherein N, A, $R_1$ and $R_2$ are as previously defined. In principle, one or more acid moieties of the phosphate may be esterified and many other combinations of phosphate and fatty alcohol substitution are possible. For example, a nucleoside monophosphate could have one or two aliphatic esters; a nucleoside diphosphate could have one to three aliphatic esters, and the nucleoside triphosphate could have one to four aliphatic esters. Nucleosides can be "chain terminating" dideoxynucleosides or other antiviral nucleosides.

Since cells contain a variety of esterases, it is anticipated that this class of compounds will be hydrolyzed to the phosphorylated nucleoside, bypassing the deficiency of dideoxynucleoside kinase in human monocytes and macrophages, and thereby restoring the antiviral activity.

4. Ceramide Antiviral Phosphonucleosides

Antiviral nucleoside phosphates can also be generated in cells after liposomal delivery of ceramide antiviral nucleoside phosphates having the general structure shown below:

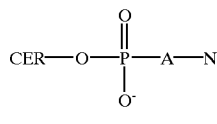

where CER is an N-acylsphingosine having the structure:

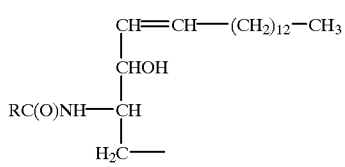

wherein R is as defined previously, or an equivalent lipid-substituted derivative of sphingosine, and N is a "chain terminating" antiretroviral nucleoside or antiviral nucleoside as previously defined. This class of compounds is useful in liposomal formulation and therapy of AIDS and other viral diseases because it can be acted upon by sphingomyelinase or phosphodiesterases in cells giving rise to nucleoside monophosphate. In addition to the compound shown above, ceramide diphosphate dideoxynucleosides can also be synthesized, which may be degraded by cellular pyrophosphatases to give nucleoside monophosphate and ceramide phosphate.

Ceramide antiviral nucleoside phosphates may be prepared in a method similar to the method for preparing antiviral nucleoside diphosphate diglycerides, with appropriate changes to the starting materials.

5. Other Lipid Derivatives of Antiviral Nucleosides

One approach to achieving even greater stability of lipid derivatives of nucleoside analogues within liposomes is by increasing lipid-lipid interaction between the lipid-nucleoside structure and the bilayer. Accordingly, in preferred embodiments, lipid derivatives of nucleoside analogues having up to four lipophilic groups may be synthesized. One class of these comprises diphosphatidylglycerol derivatives, having the general structure:

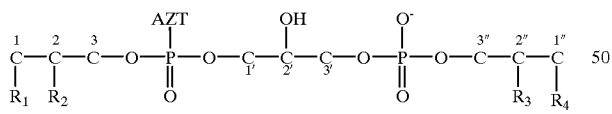

In this class, nucleosides are attached to one or both phosphates by a phosphodiester bond to the 5'-OH of the deoxyribose, ribose or dideoxyribose moiety of the antiviral nucleoside. In the case of acyclic nucleosides, such as acyclovir or gancyclovir, the link would be to the OH group equivalent to that of the ribose, deoxyribose or dideoxyribose 5'-position. There may be one or two nucleosides attached to each molecule. Nucleoside phosphates may also be attached by a pyrophosphate bond, as in Example 4.

Another class of derivatives having increased lipid components comprises bis(diacylglycero)phosphonucleotides, having the general structure:

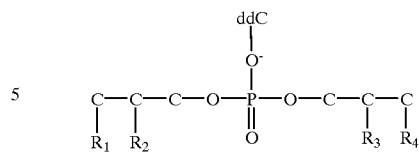

$R_{1-4}$ may be two, three or four aliphatic groups which are independently R as previously defined, said groups being in acyl ester, ether, or vinyl ether linkages. This compound may be made by the method of Example 3.

The diphosphate version of this compound, with the following structure:

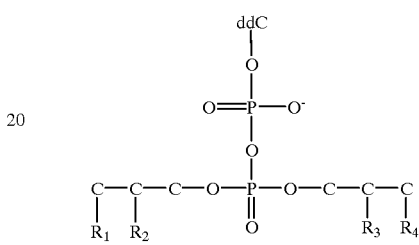

may be made by coupling the nucleoside monophosphomorpholidate to the phosphoester residue of bis(diacylglycero) phosphate according to the procedure of Example 4. This compound will be metabolized to AZT-P in the cells by CDP-diglyceride hydrolase (a pyrophosphatase). These two types of compounds may provide superior metabolic and physical properties.

Other suitable lipid derivatives of nucleosides may be synthesized using novel lipids. It is desirable, for example, to synthesize phospholipid derivatives of antiviral and anti-retroviral nucleosides which will give rise to potent antiviral agents upon alternate paths of metabolism by the target cells which take up the lipid formulation. For derivatives made up of the following types of compounds, one might anticipate a cellular metabolism distinct from that of more conventional phospholipid derivatives, because these have a phosphate group which is removed from the usual lipid group by a nitrogen containing group. The structure of these lipids features a quaternary ammonium derivative.

The compound shown:

(I)

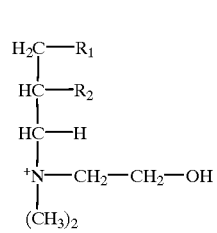

D,L, -2,3-distearoyloxypropyl (dimethyl)-p-hydroxyethyl ammonium acetate, was first synthesized by Rosenthal and Geyer in 1960 (35) and is available from Calbiochem, La Jolla, Calif. 92039. It can readily serve to link AZT-phosphate or any other antiviral nucleoside phosphate, using triisopropylbenzenesulfonyl chloride (TIBSC) as described in Example 1 or 7.

Alternatively, AZT may be linked to the phosphorylated ammonium lipid prepared by $POCl_3$, using TIBSC. Shown below is the AZT derivative of the phosphorylated compound I, D,L,-2,3-diacyloxypropyl(dimethyl)-β-hydroxyethyl ammonium acetate, where $R_1$ and $R_2$ are aliphatic groups as previously defined, of the preferred structure:

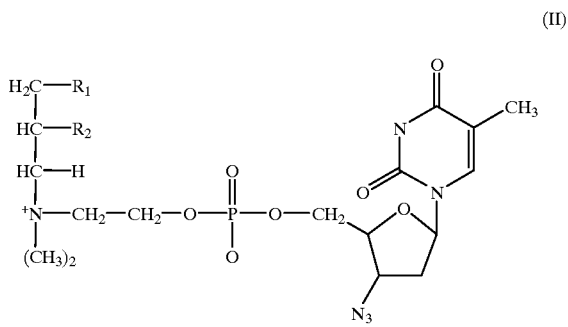

(II)

Further, the Compound I of Rosenthal and Geyer may also be phosphorylated as they describe in their paper (35). One may also use the phosphorous oxychloride method of Toorchen and Topal (20) to prepare the phosphate ester of I. To this phosphorylated species one may then couple any antiviral or antiretroviral nucleoside using the morpholidate derivative of the nucleoside phosphate as reported by Agranoff and Suomi, (21) and modified by Prottey and Hawthorne, 1967 (22). The resulting nucleoside diphosphate derivatives of I may have exemplary properties as antiviral agents delivered in liposomes to infected cells. Preferred nucleosides include, but are not limited to: AZT, ddA, ddC, ddI, acyclovir, and gancyclovir. The AZT diphosphate derivative of Compound I is shown below:

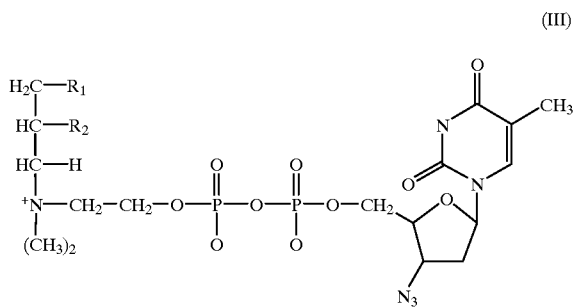

(III)

In any of the lipids derivatives described in the preceding sections 1 through 5 above, the nucleoside may be any antiviral nucleoside; $R_{1-2}$ (as well as $R_{3-4}$ for the bis (diacylglycero) species) may be any saturated or unsaturated fatty acid having from 2 to 24 carbon atoms. Polyunsaturated, hydroxy, branched chain and cyclopropane fatty acids are also possible. The stereochemistry of the glycerol moieties can include sn-1 or sn-3 phosphoester bonds or racemic mixtures thereof. There may be 1 or 2, (as well as 3, or 4 for the bis(diacylglycero) species) acyl ester groups, or alkyl ether or vinyl ether groups, as required.

A variety of other phospholipids may be linked to nucleosides, including, but not limited to phosphatidylglycerol, phosphatidylinositol, or any other phospholipid wherein the head group contains an available linking hydroxyl group, in either a natural polyhydroxyl alcohol such as inositol, or one in which it has been substituted by another polyhydroxy alcohol or by a carbohydrate, such as a sugar, again either natural or synthetic. In this case the nucleoside phosphate will be added by esterification to one or more of the hydroxyls of the alcohol or carbohydrate. Other glycolipids may also serve as the ligand to which the phosphate group of the nucleotide is attached by means of esterification to a glycolipid hydroxyl group. Other glycolipids, whether or not phospholipids, such as selected cerebrosides or gangliosides, either natural or synthetic, having suitable hydrophobic properties may also be advantageously used. These may also be linked to nucleotides by similar esterification of carbohydrate hydroxyl groups.

Furthermore, antiviral nucleosides may be linked to the phosphate groups of the phosphatidylinositol mono-, di- and triphosphates, or to the phosphate-substituted carbohydrate moieties of phospholipids or glycolipids, either natural or synthetic.

Phosphatidylserine may be linked to nucleoside analogues directly by esterification of its carboxyl group with the 5'-hydroxyl of the nucleoside ribose group. Synthetic phospholipids which are similar in structure to phosphatidylserine, containing a carboxyl group in the polar headgroup, may be linked in a similar way.

Phospholipids having alkyl chains attached by ether or vinyl ether bonds may also be used to prepare nucleotide derivatives according to the present invention. Suitable phospholipids for this purpose comprise naturally occurring acetal phosphatides, or plasmalogens, comprising a long chain fatty acid group present in an unsaturated vinyl ether linkage. Alternatively, analogs of 1-O-alkyl glycerol or 2-O-alkyl glycerol may be prepared synthetically, and linked to a selected nucleotide as described in Example 7. Derivatives of glycero-3-phospho-5'-azidothymidine are preferred, and may be prepared by condensing AZT monophosphate with various analogs of 1-O-alkyl-glycerol having an alkyl group of 2 to 24 carbon chain length at the 1 position of glycerol. The 1-O-alkyl group may consist of a saturated, unsaturated aliphatic group having a chain length of 2 to 24 carbon atoms. The 1-O-alkyl glycerol residue may be racemic or stereospecific. This compound may be acylated with fatty acid chlorides or anhydrides resulting in the synthesis of 1-O-alkyl, 2-acyl-glycero-3-phospho-5'azidothymidine. Similarly, by using a large excess of azidothymidine monophosphate, the 1-O-alkyl, 2,3-bis(phospho-5'-3'-azido, 3'-deoxythymidine)glycerol analogs may be synthesized. These derivatives have the general structure:

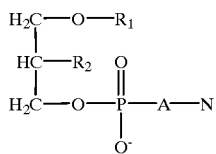

Where $R_1$ is an unsaturated or saturated alkyl chain 1 to 23 carbon atoms in length in ether or vinyl ether linkage. $R_2$ is OH or a saturated or unsaturated fatty acid ester of 2 to 24 carbon atoms. An ether or vinyl ether link at $R_2$ is also possible. The group at position 1 of glycerol may also be OH if $R_2$ is the ether linked alkyl chain. N is any antiviral nucleoside linked in a 5' phosphodiester link and A is a chalcogen (O, C or S).

Although phosphorylated antiviral nucleosides (nucleotides) are preferred embodiments of the present invention, it is possible to utilize non-phosphorus containing lipid derivatives of nucleoside analogues if it is not necessary to provide the infected cell with the nucleoside phosphate in order to achieve an antiviral effect through the processes of cellular metabolism. Some examples of compounds of this type would have fatty acids esterified, or present in alkyl linkage, directly to the 5'-hydroxyl of the nucleoside according to the synthetic method of Example 13.

Alternatively, a "spacer" molecule having, for example, carboxyl groups at either end and 0 to 10 $CH_2$ groups in the center, could be esterified to the 5'-hydroxyl of the antiviral nucleoside. The other carboxyl of the "spacer" may be esterified to the free hydroxyl of diacylglycerol or any other lipid having an available hydroxyl function. Other linking ("spacer") groups with suitable functional groups at the ends may also be used to link the diglyceride or other suitable lipid group to the nucleoside, by chemical methods well known to those skilled in the art.

Preparation of Liposomes Comprising Lipid Derivatives of Antiviral Nucleosides

After synthesis, the lipid derivative of the nucleoside analogue is incorporated into liposomes, or other suitable carrier. The incorporation can be carried out according to well known liposome preparation procedures, such as sonication, extrusion, or microfluidization. Suitable conventional methods of liposome preparation include, but are not limited to, those disclosed by Bangham, et al. (4), Olson, et al. (26), Szoka and Papahadjapoulos (27), Mayhew, et al. (28), Kim, et al. (29), Mayer, et al. (30) and Fukunaga, et al. (31).

The liposomes can be made from the lipid derivatives of nucleoside analogues alone or in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol. Synthetic phospholipids that may also be used, include, but are not limited to, dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Other additives such as cholesterol or other sterols, cholesterol hemisuccinate, glycolipids, cerebrosides, fatty acids, gangliosides, sphingolipids, 1,2-bis(oleoyloxy)-3-(trimethyl ammonio)propane (DOTAP), N-[1-(2,3-dioleoyl) propyl]-N,N,N-trimethylammonium (chloride) (DOTMA), D,L,-2,3-distearoyloxypropyl(dimethyl)-β-hydroxyethyl ammonium (acetate), glucopsychosine, or psychosine can also be added, as is conventionally known. The relative amounts of phospholipid and additives used in the liposomes may be varied if desired. The preferred ranges are from about 80 to 95 mole percent phospholipid and 5 to 20 mole percent psychosine or other additive. Cholesterol, cholesterol hemisuccinate, fatty acids or DOTAP may be used in amounts ranging from 0 to 50 mole percent. The amounts of antiviral nucleoside analogue incorporated into the lipid layer of liposomes can be varied with the concentration of their lipids ranging from about 0.01 to about 100 mole percent.

Using conventional methods to entrap active compound entraps approximately 20 to 50% of the material present in solution; thus, approximately 50 to 80% of the active compound is wasted. In contrast, where the nucleoside analogue is incorporated into the lipids, virtually all of the nucleoside analogue is incorporated into the liposome, and virtually none of the active compound is wasted.

The liposomes with the above formulations may be made still more specific for their intended targets with the incorporation of monoclonal antibodies or other ligands specific for a target. For example, monoclonal antibodies to the CD4 (T4) receptor may be incorporated into the liposome by linkage to phosphatidylethanolamine (PE) incorporated into the liposome by the method of Leserman, et al. (19). As previously described, HIV will infect those cells bearing the CD4 (T4) receptor. Use of this CD4-targeted immunoliposome will, therefore, focus antiviral compound at sites which HIV might infect. Substituting another CD4 recognition protein will accomplish the same result. On the other hand, substituting monoclonal antibody to gp110 or gp41 (HIV viral coat proteins) will focus antiviral immunoliposomes at sites of currently active HIV infection and replication. Monoclonal antibodies to other viruses, such as Herpes simplex or cytomegalovirus will focus active compound at sites of infection of these viruses.

Therapeutic Uses of Lipid Derivatives

The liposome incorporated phosphorylated nucleoside analogue is administered to patients by any of the known procedures utilized for administering liposomes. The liposomes can be administered intravenously, intraperitoneally, intramuscularly, or subcutaneously as a buffered aqueous solution. Any pharmaceutically acceptable aqueous buffer or other vehicle may be utilized so long as it does not destroy the liposome structure or the activity of the lipid nucleoside analogue. One suitable aqueous buffer is 150 mM NaCl containing 5 mM sodium phosphate with a pH of about 7.4 or other physiological buffered salt solutions.

The dosage for a mammal, including a human, may vary depending upon the extent and severity of the infection and the activity of the administered compound. Dosage levels for nucleoside analogues are well established. Dosage levels of lipid derivatives of nucleoside analogues should be such that about 0.001 mg/kilogram to 1000 mg/kilogram is administered to the patient on a daily basis and more preferably from about 0.05 mg/kilogram to about 100 mg/kilogram.

The present invention utilizes the antiviral nucleoside derivatives noted above incorporated in liposomes in order to direct these compounds to macrophages, monocytes and any other cells which take up the liposomal composition. Ligands may also be incorporated to further focus the specificity of the liposomes.

The derivatives described have several unique and novel advantages over the water soluble dideoxynucleoside phosphates described in an earlier copending application.

First, they can be formulated more efficiently. Liposomes comprising lipid derivatives of nucleoside analogues have much higher ratios of drug to lipid because they are incorporated into the wall of the liposome instead of being located in the aqueous core compartment. Secondly, the liposomes containing the lipophilic dideoxynucleoside derivatives noted above do not leak during storage, providing improved product stability. Furthermore, these compositions may be lyophilized, stored dry at room temperature, and reconstituted for use, providing improved shelf life. They also permit efficient incorporation of antiviral compounds into liposomal formulations without significant waste of active compound.

They also provide therapeutic advantages. Stability of the liposomally incorporated agent causes a larger percentage of the administered antiviral nucleoside to reach the intended target, while the amount being taken up by cells in general is minimal, thereby decreasing the toxic side effects of the nucleosides. The toxic side effects of the nucleosides may be further reduced by targeting the liposomes in which they are contained to actual or potential sites of infection by incorporating ligands specifically binding thereto into the liposomes.

Finally, the compounds noted above have been constructed in a novel way so as to give rise to phosphorylated dideoxynucleosides or other antiviral nucleosides upon further cellular metabolism. This improves their antiretroviral (antiviral) effect in monocytes and macrophages or other cells which are known to be resistant to the effects of the free antiviral compounds. Further, the compounds pre-incubated with lymphoid cells provide complete protection from HIV infection for up to and exceeding 48 hours after the drug is removed, while the free nucleoside provides no protection 24 hours after removal. Finally, the lipid compounds are expected to be useful in treating HIV infections due to strains of virus which are resistant to free antiretroviral nucleoside analogues.

Lipid derivatives of antiviral agents have a prolonged antiviral effect as compared to the lipid-free agents; therefore they provide therapeutic advantages as medicaments even when not incorporated into liposomes. Non-liposomal lipid derivatives of antiviral nucleoside analogues may be applied to the skin or mucosa or into the interior of the body, for example orally, intratracheally or otherwise by the pulmonary route, enterally, rectally, nasally, vaginally, lingually, intravenously, intraarterially, intramuscularly, intraperitoneally, intradermally, or subcutaneously. The present pharmaceutical preparations can contain the active agent alone, or can contain further pharmaceutically valuable substances. They can further comprise a pharmaceutically acceptable carrier.

Pharmaceutical preparations containing lipid derivatives of antiviral nucleosides are produced by conventional dissolving and lyophilizing processes to contain from approximately 0.1% to 100%, preferably from approximately 1% to 50% of the active ingredient. They can be prepared as ointments, salves, tablets, capsules, powders or sprays, together with effective excipients, vehicles, diluents, fragrances or flavor to make palatable or pleasing to use.

Formulations for oral ingestion are in the form of tablets, capsules, pills, ampoules of powdered active agent, or oily or aqueous suspensions or solutions. Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

The therapeutically effective amount of the lipid derivatives is determined by reference to the recommended dosages of the active antiviral nucleotide, bearing in mind that, in selecting the appropriate dosage in any specific case, consideration must be given to the patient's weight, general health, metabolism, age and other factors which influence response to the drug. The parenteral dosage will be appropriately an order of magnitude lower than the oral dose.

A more complete understanding of the invention can be obtained by referring to the following illustrative examples, which are not intended, however, to unduly limit the invention.

EXAMPLE 1

Synthesis of 1,2-Dimyristoylglycerophospho-5'-(3'-azido-3'-deoxy)thymidine, monosodium salt Preparation of Dimyristoylphosphatidic Acid (DMPA-H)

In a separatory funnel (500 ml), dimyristoylphosphatidic acid disodium salt (1 g., 1.57 mmol) was first dissolved in chloroform:methanol (2:1 by volume, 250 ml) and mixed well. Distilled water (50 ml) was added to the solution, and the pH was adjusted to 1 by adding concentrated hydrochloric acid. The solution was mixed well and the chloroform layer collected. The chloroform layer was back washed once with methanol:water (1:1 by volume, 80 ml) and evaporated under reduced pressure at 30° C. to yield dimyristoylphosphatidic acid (DMPA-H) as a white foam. Cyclohexane (10 ml) was added and the solution lyophilized to dryness to obtain a white powder (850 mg) which was then stored at −20° C. A day before the coupling reaction, DMPA-H (250 mg, 0.42 mmol) was dissolved in cyclohexane (10 ml) in a round-bottom (50 ml) flask and the solvent evaporated under reduced pressure at room temperature. This process was repeated four more times and the DMPA-H further dried in the vacuum oven at room temperature overnight over $P_2O_5$ and stored in a desiccator at −20° C.

Coupling Reaction

Under argon, to the 50 ml round-bottom flask containing dried DMPA-H (250 mg, 0.42 mmol), dried 3'-azido-3'-deoxythymidine (AZT), Sigma Chemical, St. Louis, Mo., (85 mg, 0.31 mmol, dried over $P_2O_5$ under vacuum overnight), and 2,4,6-triisopropylbenzenesulfonyl chloride (315 mg, 1.04 mmol) was added, and anhydrous pyridine (2 ml) added via syringe to obtain a clear solution. The reaction mixture was stirred at room temperature for 18 hours. (The reaction was followed by thin layer chromatography). Water (1 ml) was added to the crude product to destroy excess catalyst and the solvent was evaporated under reduced pressure to yield a yellow gum which was then redissolved in a small volume of methanol:chloroform (1:9 by volume) and applied to a column of silica gel (45 g, Kieselgel 60, West Germany). The column was eluted with 8% methanol in chloroform. After a forerun (rejected), AZT was recovered, and then dimyristoylphosphatidyl-3'-azido-3'-deoxythymidine (DMPA-AZT) was obtained. The fractions containing the product were combined and the solvent was evaporated under reduced pressure. Cyclohexane (5 ml) was added to the residue and the mixture lyophilized to dryness under vacuum over $P_2O_5$ to yield pure DMPA-AZT (270 mg, 0.29 mmol, 95%).

Conversion to Monosodium Salt

To the dried DMPA-AZT redissolved in chloroform:methanol (2:1 by volume, 30 ml), distilled water (6 ml) was added, mixed well, and the pH of the aqueous layer was adjusted to 1. The chloroform layer was collected and 10 ml of methanol:water (1:1,) was added and mixed well. The pH of the aqueous layer was adjusted to 6.8 with methanolic NaOH (0.1N N), mixed well, and the aqueous layer was maintained at pH 6.8. The combined chloroform, methanol and water mixture was evaporated under reduced pressure to yield dimyristoylphosphatidyl 3'-azido-3'-deoxythymidine monosodium salt. The residue was redissolved in chloroform:methanol (2:1 by volume, 2 ml) and acetone added to precipitate DMPA-AZT monosodium salt which was further dried from cyclohexane (5 ml) to yield a white powder (220 mg, 0.26 mmol, 78% yield based on AZT). The melting point was 230° C.; Rf value on silica gel G thin layer plates was 0.32 (chloroform:methanol:water:ammonia 80:20:1:1), Rf 0.58 (chloroform:methanol:water:ammonia 70:30:3:2), Rf 0.31 (chloroform:methanol:water 65:25:4); UV absorption maximum 266 nm ($\epsilon$ 10,800); Analysis Calculated for $C_{41}N_5O_{11}P_1H_{72}$. $1H_2O$: C,57.24; H,8.44; P,3.61; Found: C,56.80; H,8.83; P,3.52. MS, m/e 864.60 (M+)

Proton NMR: (CDCL3) $\delta$ 0.88 (6H, bt, J=6.9 Hz, acyl CH3), 1.26 (40H, s, acyl CH2), 1.60 (4H, bs, $\beta$ acyl CH2), 1.94 (3H, s, thymine CH3), 2.31 (4H, m, acyl CH2), 2.39 (2H, m, ribose 2'H), 3.38 (2H, bd, J=12.6 Hz, ribose 5'H), 3.78 (2H, m, sn-3 $CH_2$ glycerol), 4.00 (1H, dd, J1=12 Hz, J2=6 Hz, sn-1 $CH_2$ glycerol), 4.18 (1H, dd, J1=12 Hz, J2=6 Hz, sn-1 $CH_2$ glycerol), 4.07 (1H, m, ribose 3'H), 4.41 (1H, m, ribose 4'H), 5.24 (1H, m, sn-2 CH glycerol), 7.62 (1H, s, thymine 6H), 6.21 (1H, t, J=6 Hz, ribose 1'H). The peak area ratio of phosphatidic acid to AZT is 1.

EXAMPLE 2

Synthesis of 1,1,2-Dimyristoylglycerophospho-5'-(3'deoxy)thymidine, monosodium salt 3'-deoxythymidine was obtained from Sigma Chemical, St. Louis, Mo. The lipid derivative of this analogue was synthesized using the same method described above in Example 1. Melting Point 235° C., Rf on silica gel G 0.25 (chloroform/methanol/water/ammonia 80:20:1:1); 0.57 (chloroform:methanol:ammonia:water 70:30:3:2); 0.24 (chloroform:methanol:water 64:25:4); UV absorption maximum 269 nm ($\epsilon$ 8,400); Analysis: Calculated for $C_{41}N_2O_{11}P_1H_{72}Na_1.1H_2O$: C,58.53; H,8.87; P, 3.69; Found: C,56.75; H,9.33; P,3.58. MS, m/e 823.00 (M+).

Proton NMR: (CDCL3) $\delta$ 0.91 (6H, bt, J=6.8 Hz, acyl CH3), 1.23 (4H, bs, acyl CH2), 1.26 (4H, bs, acyl CH2), 1.28 (32H, bs, acyl CH2), 1.62 (4H, m, $\beta$ acyl CH2), 1.97 (3H, s, thymine CH3), 2.05 (2H, m, ribose 2'H), 2.35 (4H, m, acyl CH2), 3.39 (2H, bs, ribose 5'H), 3.90 (2H, m, sn-1 $CH_2$ glycerol), 4.16 (1H, m, sn-1 $CH_2$ glycerol), 4.24 (1H, m, sn-1 $CH_2$ glycerol), 4.38 (1H, m, ribose 4'H), 5.23 (1H, m, sn-2 glycerol) 6.10 (1H, bt, ribose 1'H), 7.68 (1H, s, thymine 6H). The peak area ratio of phosphatidic acid to 2'3'-dideoxythymidine is 1.

EXAMPLE 3

Synthesis of 1,2-Dimyristoylglycerophospho-5'-(2', 3'-dideoxy)cytidine

Preparation of 4-acetyl-2'3'-dideoxycytidine

To a stirred, refluxing solution of 2'-3'-dideoxycytidine (DDC) (400 mg, 1.89 mmol) in anhydrous ethanol (35 ml, dried first with Lindy type 4× molecular sieve, and twice distilled over magnesium turnings) was added acetic anhydride (0.4 ml, 5.4 mmol). During the course of a 3 hour refluxing period, four more additional 0.4 ml portions of acetic anhydride were added at 30 minute intervals. The reaction was followed by thin layer chromatography (silica gel F254, Kodak Chromagram, developed with 10% methanol in chloroform). After the final addition, the solution was refluxed for 1 more hour. The reaction mixture was cooled and solvent was evaporated under diminished pressure. The residue was redissolved in 8% methanol in chloroform (5 ml) and chromatographed on a silica gel column (2.2 cm×30 cm, Kieselgel 60, 70–230 mesh, EM Science, 45 g). The column was eluted with 8% methanol in chloroform to yield pure 4-acetyl-2'3'-dideoxycytidine (DDC-OAC) in 80% yield.

Coupling Reaction

A day before the coupling reaction, DMPA-H (prepared as before, 250 mg, 0.42 mmol) was dissolved in cyclohexane (10 ml) in a round-bottom flask (50 ml) and the solvent evaporated under reduced pressure at room temperature. This process was repeated four more times and DMPA-H further dried in a vacuum oven at room temperature overnight over $P_2O_5$. Under argon, to the 50 ml round-bottom flask containing dried DMPA-H was added dried (DDC-OAC) (85 mg, 0.33 mmol, dried over $P_2O_5$ under vacuum overnight), and 2,4,6-triisopropylbenzenesulfonyl chloride (315 mg, 1.04 mmol), and anhydrous pyridine (2 ml) via syringe to obtain a clear solution. The reaction mixture was stirred at room temperature for 18 hours. (The reaction was followed by thin layer chromatography). Water (1 ml) was added to the mixture to destroy excess catalyst. The solvent was evaporated under reduced pressure to yield a yellow gum which was redissolved in a small volume of methanol in chloroform (1:9 by volume) and applied to a column of silica gel (45 g, Kieselgel 60, EM Science). The column was topped with a small amount of sand (500 mg) to prevent the sample from floating during elution. The column was eluted with 8% methanol in chloroform (1.5L). After a forerun (rejected), then dimyristoylphosphatidyl-5'-(2'3'-dideoxy) cytidine (DMPA-DDC) was obtained. The fractions containing the product were combined and the solvent was evaporated under reduced pressure. The residue was further dried with cyclohexane to yield pure DMPA-DDC-OAC (210 mg, 0.21 mmol, in 70% yield). $R_f$ 0.40 (silica gel GF, 20×20 cm, Analtech, chloroform:methanol:water: ammonia 80:20:1:1 by volume).

Deblocking with 9N NH4OH

DDC-OAC-DMPA (40 mg, 0.04 mmol) was dissolved in chloroform:methanol (1:1, 2 ml), and 9N $NH_4OH$ (10 drops) was added at once. The solution was stirred at room temperature for 15 minutes and was then quickly neutralized with glacial acetic acid to pH 7. The neutralized solution was evaporated to dryness overnight under reduced pressure to yield dimyristoylphosphatidyl 5'(2'3'-dideoxy)cytidine (DMPA-DDC, 35 mg, 0.037 mmol). Melting point: DMPA-ddC decomposed at 240° C. On thin layer chromatography on silica gel GF plates, the Rf values were: 0.11 (chloroform:methanol:water:ammonia 80:20:1:1); 0.38 (chloroform:methanol:ammonia:water 70:30:3:2); 0.15 (chloroform:methanol:water 65:25:4); UV absorption maximum 273 nm ($\epsilon$ 5,800).

NMR: (CDCL3) $\delta$ 0.86 (6H, by, acyl CH3), 1.24 (40H, bs, acyl CH2), 1.57 (4H, m, $\beta$ acyl CH2), 2.28 (4H, m, acyl CH2), 3.36 (2H, m, ribose 5'H), 3.94 (2H, bs, sn-3 CH$_2$ glycerol), 4.19 (1H, m, sn-1 CH$_2$ glycerol), 4.29 (1H, m, sn-1 CH$_2$ glycerol), 4.40 (1H, bs, ribose 4'H), 5.19 (1H, m, sn-2 CH glycerol), 5.89 (1H, m, thymine 5-H), 7.44 (1H, bs, thymine NH3), 7.94 (1H, bs, thymine NH$_2$). The peak area ratio of phosphatidic acid to 2'3'-dideoxycytidine is 1.

EXAMPLE 4

Synthesis of (3'Azido-3'-deoxy) thymidine-5'-diphosphate-sn-3-(1,2-dipalmitoyl)glycerol Synthesis of AZT-monophosphate Morpholidate This compound was synthesized following the method of Agranoff and Suomi (21). AZT-monophosphate was converted into the acidic form by passing a solution in water through a column of Dowex 50W (50×2–200, 100–200 mesh, Sigma Chemicals, St. Louis, Mo.). A solution of 117 mg AZT-monophosphate (0.3 millimoles) in 3 ml of water was transferred to a two neck round bottom flask. The 3 ml of t-butanol and 0.106 ml of freshly distilled morpholine (1.20 millimoles) were added and the mixture was placed in a oil bath at 90° C. Four equivalents of dicyclohexylcarbodiimide 249 mg, 1.20 millimole) in 4.5 ml of t-butanol were added dropwise. The reaction was monitored by thin layer chromatography on silica gel 60, F 254, plates (E. Merck, Darmstadt) with chloroform/methanol/acetic acid/water (50/25/3/7 by volume) as the developing solvent. The reaction was noted to be complete after 3 hours. The mixture was cooled and after addition of 4.5 ml of water was extracted four times with 15 ml of diethylether. The aqueous layer was evaporated to dryness and dried in vacuo over P$_2$O$_5$. The product was obtained (199 mg, 100% yield) and used for coupling to phosphatidic acid without further purification.

Coupling of AZT-monophosphate Morpholidate to Dipalmitoylphospatidic Acid

Dipalmitoylphosphatidic acid, disodium salt was converted to the free acid by extracting the material from chloroform by the method of Bligh and Dyer (34) using 0.1N HCl as the aqueous phase. The chloroform layer was evaporated to dryness in vacuo, the phosphatidic acid (196 mg, 0.3 millimoles) was redissolved in chloroform and transferred to the vessel containing the AZT-monophosphate morpholidate. After the chloroform was removed in vacuo using a rotary evaporator, the mixture was dried by addition and evaporation of benzene and finally dried in vacuo over P$_2$O$_5$. The reaction was started by addition of 30 ml of anhydrous pyridine and the clear mixture was stirred at room temperature. The reaction was monitored with thin layer chromatography as noted above with chloroform/methanol ammonia/water (70/38/82 by volume) as developing solvent. The Rf of phosphatidic acid, AZT-monophosphate morpholidate and AZT-diphosphate dipalmitoylglycerol is 0.11, 0.50, and 0.30, respectively.

After 70 hours the pyridine was evaporated and the product was extracted into chloroform after addition of 15 ml of water, 30 ml of methanol, 22 ml chloroform and sufficient 1N formic acid to adjust the pH to 4.0. The combined chloroform layers after two extractions were evaporated to dryness, the residue was dissolved in chloroform/methanol/ammonia/water, 70/38/8/2, and the product was purified by silica gel column chromatography in this solvent applying an air pressure equivalent to one meter of water. Fractions not completely pure were further purified by HPLC on a reverse phase column (vydac C18) using water/methanol (8/2 by volume) and methanol as eluents. Fractions containing the desired product were evaporated to dryness to give 132 mg. of a white solid (44% yield) which gave a single spot by thin layer chromatography with silica gel g plates developed with chloroform/methanol/ammonia/water, 70/38/8/2 (Rf 0.35) and chloroform/methanol/water, 65/35/4 (Rf 0.54).

500 MHz NMR (CDCl$_3$) δ 0.88 (3H, t, J=6.93 Hz, sn-2-acyl CH$_3$), 0.92 (3H, t, J=7.48 Hz, sn-1-acyl chain CH$_3$), 1.25 (48H, s, CH$_2$ acyl chains), 1.55 (4H, bs, β CH$_2$ acyl chains) 1.83 (3H, s, CH$_3$ thymine), 2.25 (2H, t, J=6.97 Hz, 2H, alpha CH$_2$ sn-2-acyl chain), 2.27 (2H, t, J=7.79 Hz, CH$_2$ sn-1-acyl chain), 2.44 (4H, bs, 2' and 5' H ribose), 3.78 (1H, dd, J=1.68, 5.51 Hz, 3'H ribose), 3.95 (2H, bs, sn-3 CH$_2$ glycerol), 4.07 (1H, bs, He/$_a$ sn-1 CH$_2$ glycerol), 4.13 (1H, bs, 1H, sn-2 CH glycerol), 4.36 (1H, bs, H/$_a$/H$_e$ sn-1 CH$_2$ glycerol), 5.21 (1H, bs, sn-2 CH glycerol), 5.66 (1H, bs, 1'H ribose), 7.14 (1H, d, J=6.25 Hz, 6H thymine). The ratio of acyl chains: glycerol:ribose: thymine as deduced from appropriate resonances amounted to 2.12:0.93:0.98:1.00. IR (KBr, disk) showed 2105 (azido), 1745 (c=o ester) and 1705 (c=o thymine) as identifiable bands.

EXAMPLE 5

Synthesis of an Antiviral Nucleoside Diacyl Phosphate

Dihexadecyl phospho-5'-dideoxycytidine is synthesized according to the method described in Example 1, except that the reactants are dideoxycytidine and dihexadecyl hydrogen phosphate. The starting material dihexadecyl hydrogen phosphate is synthesized from hexadecan-1-ol and phenyl phosphorodichloridate as first reported by D. A. Brown, et al. (32).

EXAMPLE 6

Synthesis of Dideoxyadenosine Diphosphate Ceramide an Antiviral Phosphonucleoside The method of Example 2 is repeated, except that dideoxyadenosine monophosphate morpholidate is substituted for the dideoxycytidine monophosphate morpholidate. Ceramide phosphoric acid is prepared by the action of phosphorus oxychloride on ceramide. Ceramide phosphoric acid is substituted for the dimyristoyl phosphatidic acid. Similar results are obtained.

EXAMPLE 7

Synthesis of 1-O-stearoylglycero-rac-3-phospho-5'-(3'-deoxy, 3,-azido)thymidine

Dry 1-O-stearoyl-rac-3-glycerol (batyl alcohol, 250 mg), 3'-azido-3'deoxythymidine monophosphate sodium salt (0.725 gm) and 2,4,6,-triisopropylbenzenesulfonyl chloride (TPS, 1.219 gm) were mixed in dry pyridine and stirred overnight under nitrogen. Chloroform (50 ml) was added and the reaction mixture was washed twice with cold 0.2N HCl and 0.2N sodium bicarbonate. The organic phase was removed in vacuo with a rotary evaporator and the product was crystallized at −20° C. from 20 ml of chloroform/acetone (12:8 by volume). The final purification of the compound was done by preparative thin layer chromatography using 500 micron layers of silica gel G developed with chloroform/methanol/concentrated ammonia/water (70/30/1/1 by volume).

In the preceding syntheses, proton NMR spectra were obtained with a General Electric QE-300 spectrometer, using tetramethylsilane as internal standard (key: s=singlet, d=doublet, t=triplet, q=quartet, dd=doublet of doublets, b=broad), UV spectra were recorded on Shimadzu UV-160, spectrophotometer. Fast atom bombardment mass spectra were determined by Mass Spectrometry Service Laboratory, University of Minnesota. Elemental analyses were determined by Galbraith Laboratories, Knoxville, Tenn. and Schawarzkopf Microanalytical Laboratory, N.Y. Melting points were obtained with a Fisher-Johns melting apparatus. Column chromatography was carried out on Merck silica gel 60 (70–230 mesh). Rf values were obtained with HPTLC Merck, Kieselgel 60 pre-coated plates, 10×10 cm. Anhydrous pyridine, 2,4,6-Triisopropylbenzenesulfonyl chloride (TPS), and 3'-azido-3'-deoxythymidine (AZT) were purchased from Aldrich. Dimyristoylphosphatidic acid, disodium salt, was purchased from Avanti; batyl alcohol was obtained from Sigma Chemical, St. Louis, Mo.

EXAMPLE 8

Preparation of Liposomes Containing Antiretroviral Liponucleotides 6.42 micromoles of dioleoylphosphatidylcholine, 3.85 micromoles of cholesterol, 1.28 micromoles of dioleoylphosphatidylglycerol and 1.28 micromoles of dimyristoylphosphatidyl-azidothymidine were mixed in a sterile 2.0 ml glass vial and the solvent was removed in vacuo in a rotary evaporator. In some experiments, dimyristoylphosphatidylazidothymidine was replaced with either dimyristoylphosphatidyldideoxythymidine, dimyristoylphosphatidyldideoxycytidine or azidothymidine diphosphate dimyristoylglycerol; control liposomes were prepared by omitting the antiviral liponucleotide. The dried film was placed under high vacuum overnight at room temperature to remove traces of solvent. The lipid film was hydrated at 30° C. with 0.3 ml of sterile 10 mM sodium acetate buffer (pH 5.0) containing isotonic dextrose and the ampule was sealed. The mixture was vortexed intermittently for 10 minutes followed by sonication using a Heat Systems Ultrasonics sonicator with a cup horn generator (431B) at output control setting #9 for 90 to 120 minutes at which time the sample is clarified. This sonicated preparation was diluted with sterile RPMI buffer and added to the tissue culture wells at the concentration indicated.

EXAMPLE 9

Coupling of Monoclonal Antibodies to CD4 to an Antiviral Lipid-containing Liposome Dimyristoylphosphatidyl-AZT produced by the method of Example 1, dimyristoylphosphatidylcholine, cholesterol and dimyristoylphosphatidylethanolamine in a molar ratio of 39:39:20:2. 200 mg of this lipid mixture was dried in vacuo using a rotary evaporator to form a thin film in a 100 ml round-bottom flask. 1 ml of sterile phosphate buffered saline was added and the mixture shaken gently at 20° C. for 20 minutes, followed by ten 30-second cycles of vortexing to form multilamellar liposomes. The suspension was subjected to 5 cycles of extrusion through two stacked Nucleopore polycarbonate filters having pore diameters of 200 nm to produce a homogeneous liposomal population. Other methods may be used such as sonication, reverse phase evaporation and use of a French press or Microfluidizer (Microfluidics, Newton, Mass.) 0.1 to 2 mg of OKT4a monoclonal antibodies to CD4 antigen are thiolated by incubation with 0.08 mM N-succinimidyl 3-(2-pyridyldithio)propionate (SPDP). Untreated SPDP is removed by gel filtration through Sephadex G25. The voiding DTP-protein is reduced with 0.05 M dithiothreitol in 0.1 M acetate buffered saline at pH 4.5 for 20 minutes, producing reduced thiolated antibody.

Liposomes produced by the method of Example 5, representing 5 micromoles of phospholipid are incubated overnight at room temperature with 1 mg of thiolated antibody in 0.20 ml of isotonic MES/HEPES buffer, pH 6.7. The resulting immunoliposomes are purified by the discontinuous metrizimide gradient method of Heath et al. (33) and sterilized by passage through 200 nm filters.

EXAMPLE 10

Inhibition of HIV Replication in Tissue Culture Cells by Lipid Nucleoside Conjugates A. Methods Viral Infection of Human T-cells The human T lymphoblastoid cell line, CCRG-CEM (hereafter referred to as CEM), was grown in RPMI 1640 medium containing 100 U/ml penicillin G, 100 ug/ml streptomycin, 2 mM glutamine and 10% fetal bovine serum (Hyclone Laboratories, Logan, Utah). Cells were infected with the LAV-1 strain (L. Montagnier, Paris, France) at a multiplicity of infection of one tissue culture 50% infectious dose $(TCID_{50})$/cell for 60 minutes at 37° C. in medium containing 1% polybrene. CEM cells were infected in suspension at $6 \times 10^4$ cells/ml, washed three times by centrifugation and resuspension and then distributed in 96-well plates at $6 \times 10^4$ cells/well before addition of medium containing the liposomal antiretroviral liponucleotide drugs.

Antiviral Activity as Determined by HIV P24 Assay

Antiviral activity was assayed after 3 days by the inhibition of the production of HIV p24 (gag) antigen in the cell free culture medium of the infected cells exposed to different concentrations of drug; p24 antigen was measured by ELISA (Abbott Laboratories, Chicago, Ill.) according to the manufacturer's instructions. The data are the average of two determinations and are expressed as percentage of a control incubated in the absence of drugs.

B. Experiment H533-1: FIG. 1

Liposomes containing 10 mole percent of either dimyristoylphosphatidylazidothymidine (LN1), dimyristoylphosphatidyldideoxythymidine (LN2) or azidothymidine diphosphate dimylristoylglycerol (LN4) in the indicated concentrations were tested for their ability to inhibit HIV replication in CEM (wild type) cells in vitro. All three of these antiretroviral liponucleotides inhibited HIV p24 production; the amounts of drug required to reduce virus production by 50% (E.D. 50) were as follows:

| | |
|---|---|
| Phosphatidylazidothymidine (LN1) | 2 uM |
| Phosphatidyldideoxythymidine (LN2) | 30 uM |
| AZT diphosphate dimyristoylglycerol (LN4) | 8 uM |

This demonstrates that the lipid derivatives of antiretroviral nucleotides can enter CEM cells and be converted to active nucleoside as predicted. The control liposomes (CONT) which did not contain any antiretroviral nucleotide had no effect on p24 production by CEM cells.

Figure 2:
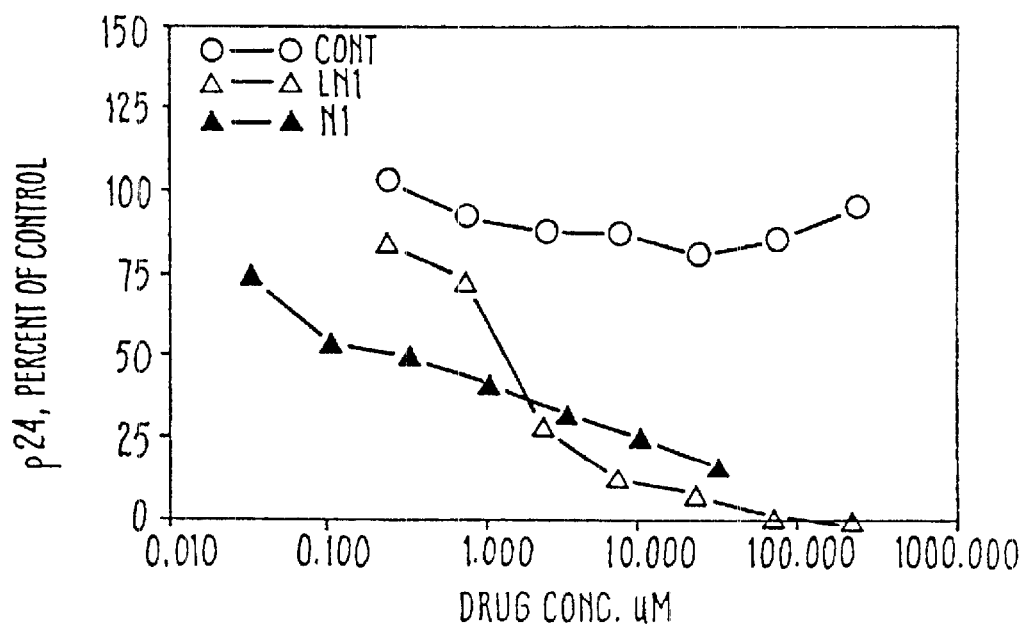

C. Experiment H747-1a: FIG. 2

Dimyristoylphosphatidylazidothymidine in liposomes (LN1) was compared with free azidothymidine (N1). At low concentrations below 0.1 uM free AZT was more effective than the liponucleotide. At concentrations ranging from 2 to 170 uM the phosphatidylAZT liposomes were more effective than the free AZT. Control liposomes (CONT) containing only inactive lipids as noted in methods were ineffective in reducing p24.

Figure 3:
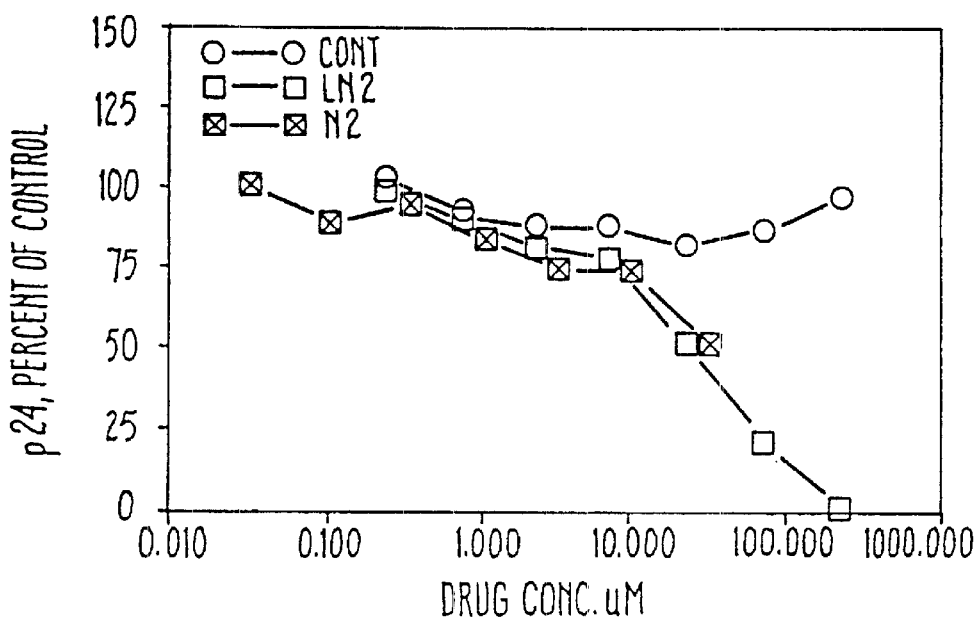

D. Experiment H747-1b: FIG. 3

Dideoxythymidine (N2) is a weak inhibitor of HIV p24 production. Surprisingly, phosphatidyldideoxythymidine (LN2) is somewhat more effective than the free nucleoside. As can be seen in the chart, slightly more free ddT is required to reduce p24 production than with phosphatidyldideoxythymidine. Control liposomes (CONT) at a matched total phospholipid concentration are without effect.

Figure 4:
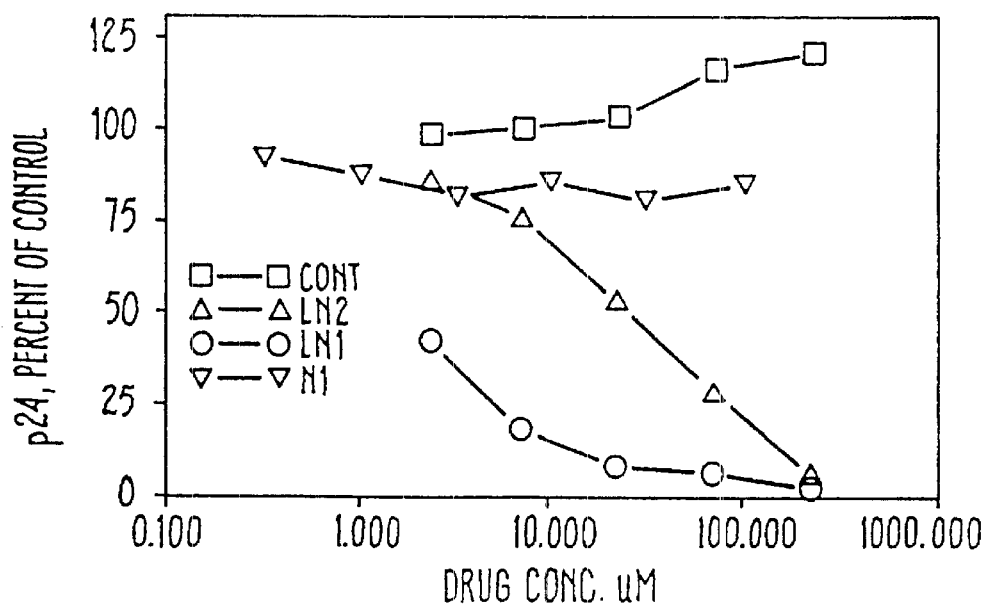

E. Experiment H637-1b: FIG. 4

In this experiment, CEM cells were replaced with mutant cells (provided by Dr. Dennis Carson, Scripps Clinic, San Diego, Calif.) which lack the thymidine kinase enzyme (CEM tk-). These cells are unable to phosphorylate thymidine derivatives and AZT is therefore inactive since it cannot be converted to the active triphosphate derivative which is needed to inhibit HIV p24 replication. As shown in the chart, AZT (N1) is completely without effect on p24 production over a wide range of concentrations (0.2 to 100 uM). However, both phosphatidylAZT (LN1) and phosphatidylddT (LN2) were capable of reducing p24 production, proving that these compounds are metabolized in the cell to the nucleoside-monophosphate which can be further activated to the triphosphate by other cellular enzymes. This data provides proof of the principles outlined in the patent which predict direct metabolism to the nucleoside monophosphate.

Figure 5:
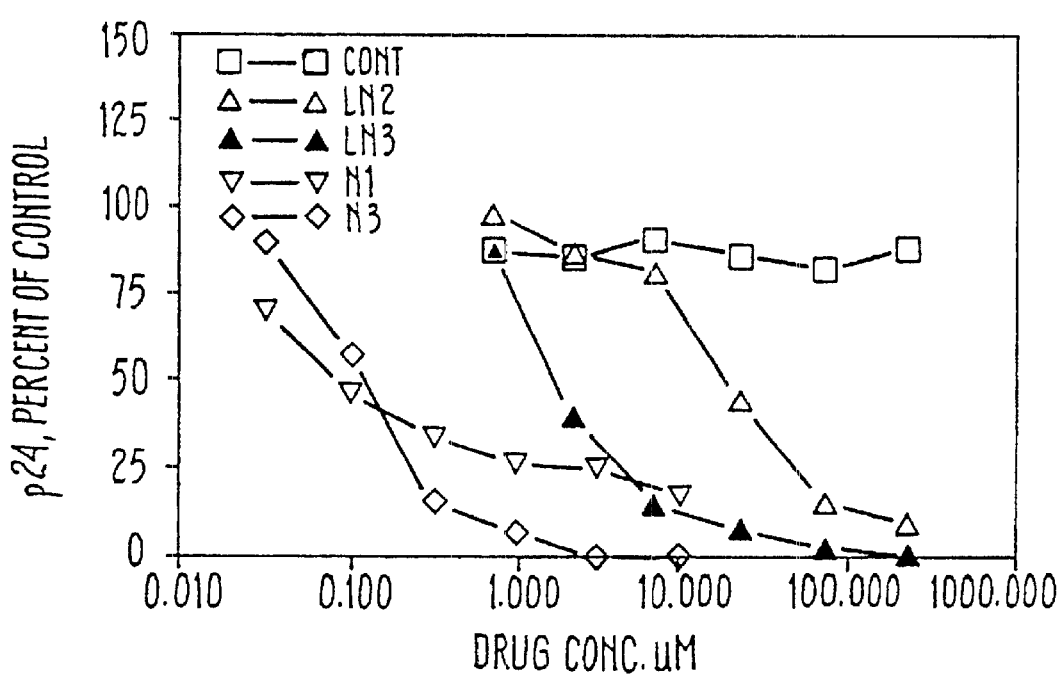

F. Experiment H805-1: FIG. 5

In this experiment dimyristoylphosphatidyldideoxycytidine (LN3) and dimyristoyldideoxythymidine (LN2) were compared with the effects of free AZT (N2) and dideoxycytidine (N3) in CEM (wild type) cells in vitro. PhosphatidylddC was the most potent liponucleotide ($ED_{50}$ 1.1 uM) and phosphatidylddT was less active as noted before ($ED_{50}$ 20 uM). Free liposomes without added antiretroviral nucleotide (CONT) were inactive.

G. Experiment I276:

In this experiment, antiviral protection provided by preincubation with dimyristoylphosphatidylazidothymidine (LN1) in liposomes prepared as noted above was compared with that of free azidothymidine (N1). CEM (wild type) cells were preincubated for 3 days under standard conditions in RPMI media containing 7.14 $\mu$M of either free AZT (N1) or phosphatidylAZT (LN1). The cells were then washed twice with PBS, and fresh RPMI media added. Each group of cells was then divided into three batches. One batch was immediately infected with HIV, as noted above; after washing away unattached HIV, the sample was allowed to incubate in media alone for 3 days. Two other batches were allowed to incubate in media alone for either 24 or 48 hours to allow any intracellular antiviral agent present to become depleted. Then they were infected with HIV, the cells washed free of virus, and fresh RPMI media added. After 3 days of further incubation, the supernates of all batches were tested for the presence of p24 protein.

Control Cells: CEM cells were subjected to HIV infection without preincubation; drug was added following HIV infection as indicated, and the cells were incubated for 3 days.

Preincubated Cells: CEM cells were preincubated for 3 days with media containing AZT (N1) or phosphatidyl AZT (LN1); after 3 days the cells were washed, subjected to HIV infection followed by addition of media without drugs. After a further incubation for 3 days, p24 was measured.

Results

| CEM Controls: No Preincubation | p24: ng/ml after 3 days incubation |
|---|---|
| HIV infection only | 204; 207 |
| HIV + 7.14 $\mu$M Azidothymidine (N1) | 64; 69 |
| HIV + 7.14 $\mu$M PhosphatidylAZT (LN1) | 16; 16 |

| CEM Preincubated Cells | Pre-Infection Interval without Drug | p24: ng/ml after 3 days incubation |
|---|---|---|
| 7.14 $\mu$M Azidothymidine (N1) | 24 h | 404; 433 |
|  | 48 h | 271; 245 |
| 7.14 $\mu$M PhosphatidylAZT(LN1) | 24 h | 6; 7 |
|  | 48 h | 4; 15 |

After a 3 day preincubation, followed by 48 hours of incubation in normal media after removal of the drugs, phosphatidylAZT provided complete protection from HIV replication as assessed by the reduced p24 production. However, AZT preincubation failed to protect the cells from HIV infection 24 and 48 hours after removal of the drug.

H. Experiment J45:

In this experiment the compound of Example 7 (1-0-stearoylglycero-rac-3-phospho-5'-(3'-deoxy, 3'-azido) thymidine) was incorporated into liposomes containing 10 mole percent of the liponucleotide as indicated in Example 8. This material was diluted with RPMI medium to the desired concentration and added to HT4-6C cells (CD4+ HeLa cells) obtained from Dr. Bruce Chesbro of the Rocky Mountain National Laboratories (Hamilton, Mont.) which had been infected with LAV-1 as noted earlier in this example. After a 3 day incubation at 37° C., the cells were washed with PBS, fixed and stained with crystal violet and the plaques were counted. The results are shown below.

| Liponucleotide Concentration | Plaques, Average | % of Untreated Control |
|---|---|---|
| 10 $\mu$M | 1 | 2 |
| 3.16 | 7 | 13 |
| 1.0 | 16 | 29 |
| 0.316 | 32 | 58 |
| 0.100 | 39 | 71 |
| 0.0316 | 43 | 78 |
| 0 | 57 | — |

The data show that 1-0-stearoyl-rac-3-phospho-5'-(3'-deoxy, 3'azido) thymidine is effective in inhibiting HIV plaque formation in HT4-6C cells infected with LAV-1. The concentration require to produce 50% inhibition is about 0.35 micromolar.

EXAMPLE 11

Synthesis of Phosphatidylacyclovir and Efficacy in Herpes Simplex Virus-Infected WI-38 Cells Dimyristoylphosphatidic acid (disodium salt) was obtained from Avanti Polar Lipids, Birmingham, Ala., and converted to the free acid (DMA-H) as described above in Example 1. Acycloguanosine (acyclovir, Zovirax®) was obtained from Sigma Chemical Co., St. Louis, Mo. and 73 mg (0.32 mmol) was dried overnight over phosphorus pentoxide in a vacuum oven. 250 mg of DMPA-H (0.42 mmol) was added to a 50 ml round bottom flask and dried overnight over phosphorus pentoxide in a vacuum oven. Under dry argon, 73 mg of acycloguanosine, 315 mg (1.04 mmol) of triisopropylbenzenesulfonly chloride (Aldrich, Milwaukee, Wis.) and 2 ml of dry pyridine (Aldrich, Milwaukee, Wis.) were added to the round bottom flask. The reaction mixture was stirred at room temperature for 18 hours followed by the addition of 1 ml of distilled water.

The solvent was evaporated in vacuo to yield a yellow gum which was redissolved in a small volume of chloroform/methanol (9/1) and applied to a column of silica gel (45 gm: Kieselgel 60, EM Science, Cherry Hill, JN). The column was eluted with 8% methanol in chloroform (500 ml), 10% methanol in chloroform (250 ml) followed by 15% methanol in chloroform (1.5 L). After a 1.5 liter forerun rejected), dimyristoylphosphatidylacycloguanosine (pACV) was obtained. Three fractions were collected and analyzed: fraction 1 (200 ml, 130 mg pACV) continued pure pACV; fraction 2 (200 ml, 150 mg) and fraction 3 (200 ml, 50 mg) contained pACV and small amounts of starting material as impurities. Fraction 1 was concentrated in vacuo and to the residue was added 5 ml of cyclohexane; the solution was frozen and lyophilized to dryness under phosphorus pentoxide to yield pure phosphatidylacycloguanosine (80 mg, 0.1 mmol).

The purified compound gave a single spot with an Rf of 0.29 when applied to K6G silica gel plates (Whatman International, Maidstone, England) developed with chloroform/methanol/water/ammonia (70/30/1 by volume). The UV absorption was maximal at 256 nm (extinction coefficient=$8.4 \times 10^3$ in $CHCl_3$). The percentage phosphorus was 3.30% (theoretical 3.89%) and the melting point was 245° C. On HPLC analysis, phosphatidylacycloguanosine gave a single peak with a retention time of 11 minutes (Spheri-5; Brownlee Labs, Applied Biosystems, Santa Clara, Calif.) when eluted with a mobile phase of 1-propanol/0.25 mM potassium phosphate/hexane/ethanol/acetic acid (245/179/31/50/0.5 by volume) at a flow rate of 0.5 ml/min.

Cell Cultures

Wi-38 cells were obtained from American Type Culture Collection (Rockville, Md. 20852) and grown in Dulbecco's minimum essential medium (DMEM) with 10% fetal calf serum (FCS). The cells were grown in 250 cm square bottles until reaching confluence.

Virus

Herpes simplex virus (HSV) type 1 (HSV-1) and type 2 (HSV-2) were obtained from the American Type Culture Collection. Both virus stocks were prepared in Wi-38 cells; extensive cytopathic effects (CPD) were observed when the stock virus was harvested by a single freezing and thawing and the cell debris was clarified by low speed centrifugation (2000 rpm). Supernatant fluids containing the virus were aliquoted into small vials and stored at −80 C. Both HSV-1 and HSV-2 stocks were titered in Wi-38 cells before use in the experiments.

Herpes Simples Virus Plague Reduction Assay

The plaque reduction assay was used to measure the antiviral effect of phosphatidylacyclovir or free ACV. Wi-38 cells were trypsinized with 0.25% trypsin for 5 min. The cells were harvested and centrifuged to remove residual trypsin and the cell pellet was resuspended in DMEM with 10% FCS. The Wi-38 cells were plated in a 96 well plate (5×10 cells/well) for one hour. The infected cells were then treated with phosphatidylacyclovir or ACV. The antiviral agents were prepared in stock solutions which were then diluted two-fold with 2% FBS in DMEM containing 0.5% methylcellulose. 100 μl of each diluted antiviral agent was added into each well of HSV infected cells.

The control and drug-treated cell cultures were incubated in a 37° C. incubator with 5% carbon dioxide for 24 hours. When HSV-infected cells (control without antiviral agent) showed readable number of plagues, the entire plate was fixed with methanol and stained with 1% crystal violet for 10 min. The dye was rinsed off with tap water and the plate was dried and plaques were counted. The antiviral effect of ACV or phosphatidylacyclovir was determined by measurement of plaque reduction as shown in the example below.

Results

Effect if Acyclovir and Phosphatidylacyclovir on Plaque Formation by HSV-1 IN WI-38 Cells

|  | 1 | 2 | mean | % no Drug |
|---|---|---|---|---|
| Acyclovir conc |  |  |  |  |
| 10 uM | 0 | 0 | 0 | 0 |
| 5 | 0 | 0 | 0 | 0 |
| 2.5 | 0 | 0 | 0 | 0 |
| 1.25 | 4 | 3 | 3.5 | 13 |
| 0.625 | 8 | 6 | 7 | 26 |
| 0.31 | 17 | 19 | 20 | 65 |
| 0.155 | 18 | 22 | 20 | 73 |
| 0 | 20;30 | 30;30 | 27.5 | 100 |
| PhosphatidylACV |  |  |  |  |
| 214 uM | toxic | toxic | — | — |
| 107 | 0 | 0 | 0 | 0 |
| 54 | 0 | 0 | 0 | 0 |
| 27 | 2 | 3 | 2.5 | 9 |
| 13.4 | 4 | 6 | 5 | 18 |
| 6.7 | 6 | 9 | 7.5 | 27 |
| 3.3 | 10 | 12 | 11 | 40 |
| 1.67 | 17 | 20 | 18.5 | 67 |
| 0.84 | 24 | 26 | 25 | 91 |
| 0 | 20;30 | 30;30 | 27.5 | 100 |

The data shown above indicate that phosphatidylacyclovir is effective in HSV-1 infected Wi-38 cells. the concentration which produces 50% inhibition is 2 uM versus 0.4 uM for acyclovir. Similar results were obtained with HSV-2 in infected Wi-38 cells.

EXAMPLE 12

Synthesis of 5'-palmitoyl(3'-deoxy-3'-azido) thymidine 0.5 grams of AZT (1.87 mmol) was dissolved in 10 ml of dry chloroform and 2 ml of dry pyridine. 0.78 grams (2.8 mmol) of palmitoyl chloride (Aldrich Chemicals, Milwaukee Wis.) dissolved in 5 ml of dry chloroform was added slowly over a period of 20 minutes at 4° C. and the reaction mixture was allowed to warm to room temperature with stirring. After 20 hours the reaction was stopped with the addition of 8 ml of distilled water, and 38 ml of chloroform/methanol/0.5N HCl (1/2/0.8 by volume) was added. The phases were separated by the addition of 10 ml of chloroform and 8 ml of 0.5N HCl. The organic phase containing the required compound was further washed with 0.5N sodium bicarbonate. The lower chloroform phase was dried over anhydrous sodium sulfate and evaporated under vacuum. The compound was crystallized from chloroform/acetone at −20° C. Further purification was obtained by silicic acid column chromatography, and 145 mg of pure 5'-palmitoyl(3'-azido, 3'-deoxy)thymidine was obtained (yield 15.3%). Elemental analysis: Predicted C 61.59, H 8.5, N 13.8 and 0 15.8; Found C 60.74, H 8.6, N 13.5 and 0 17.9. Rf on silica gel G thin layer chromatography plates: 0.92 (chloroform/methanol/ammonia/water, 70/30/1/1); 0.83 (hexane/ethylether/acetic acid, 80/20/1) and 0.86 (chloroform/acetone, 94/6), m.p. 77–80° C. $^{UV}max$ 265.

Efficacy of PalmitoylAZT in HIV-Infected HT4-6C Cells

PalmitoylAZT was incorporated into liposomes as noted in Example 8 and incubated with LAV-1 infected HT4-6C cells as noted in Examples 10 and 11. 0.8 uM palmitoylAZT inhibited plaque formation by 25% (134 plaques versus 176 in the untreated control).

It should be apparent from the foregoing that other nucleoside analogues and phospholipid derivatives thereof can be substituted in the Examples to obtain similar results. AZT-monophosphate or other antiviral nucleoside phosphate may also be contained in the aqueous compartments of the liposome. The molar percentage of the lipid antiviral nucleoside may vary from 0.1 to 100% of the total lipid mixture. Furthermore, mixtures of antiviral nucleoside lipids may be used in constructing the liposomes for therapy of viral diseases. It should be further emphasized that the present invention is not limited to the use of any particular antiviral nucleoside analogue; rather, the beneficial results of the present invention flow from the formation of liposomes from the lipid derivatives of these materials. Thus, regardless of whether an antiviral nucleoside is presently known, or whether it becomes known in the future, the methods of forming the presently-contemplated lipid derivatives therefrom are based on established chemical techniques, as will be apparent to those of skill in the art, and their incorporation into liposomes is broadly enabled by the preceding disclosure. It should be emphasized again that the present syntheses are broadly applicable to formation of compounds from essentially all nucleoside analogues for use in the practice of the present invention.

Accordingly, the invention may be embodied in other specific forms without departing from it spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced with their scope.

References

1. Richman, D. D., Kornbluth, R. S. and Carson, D. A. (1987) J. Exp. Med., 166: 1144–1149.
2. Fischl, M. S., Richman, D. D., Grieco, M. H., et al., (1987) New Eng. J. Med., 317: 185–191.
3. Richman, D. D., Fischl, M. A., Grieco, M. H., et al., (1987) New Eng. J. Med., 317: 192–197.
4. Bangham, A. D., Standish, M. M. and Watkins, J. C. (1965) J. Mol. Biol., 23: 238–252.
5. Black, C. D. V., Watson, G. J. and Ward, R. J. (1977) Trans. Roy. Soc. Trop. Med. Hyg., 71: 550–552.
6. Alving, C. R., Steck, E. A., Chapman, W. L., Waits, V. B., Hendricks, L. D. Swartz, G. M. and Hanson, W. L. (1978) Proc. Natl. Acad. Sci. USA 75: 2959–2963.
7. Lopez-Berestein, G. (1986) Ann. Int. Med., 103: 694–699.
8. Herman, E. H., Rahman, A., Ferrans, V. J. Vick, J. A. and Shein, P. S. (1983) Cancer Res., 43: 5427–5432.
9. Ostro, M. (1987) Sci. Am. 256: 103–111.
10. Salahuddin, S. Z., Rose, R. M., Groopman, J. E., Markham, P. D. and Gallo, R. C. (1985) Blood, 68: 281–284.
11. Koenig, S., Gendelman, H. E., Orenstein, J. M. Dalcanto, M. C. Pezeshkpur, G. H., Yungbluth, M. Janotta, F., Aksmit, A., Martin, M. A. and Fauci, A. S. (1986) Science, 233: 1089–1093.
12. Post, G., Kirsch, R. and Koestler, T. (1984) in Liposome Technology, Vol. III, G. Gregoriadis, Ed., CRC Press, Boca Raton, p. 1–28.
13. Scherphof, G. (1986) in Lipids and Biomernbranes, Past, Present and Future, op den Kamp, J., Roelofsen, B. and Wirtz, K. W. A., Eds., Elsevier North Holland, Amsterdam, p. 113–136.
14. Norley, S. G., Huang, L. and Rouse, B. T. (1987) J. Immunol., 136: 681–685.
15. Kond, M., Alving, C. R., Rill, W. L., Swartz, G. M. and Cannonico, P. P. G. (1985) Antimicrob. Agents Chemother. 27: 903–907.
16. Matsushita, T., Ryu, E. K., Hong, C. I. and MacCoss, M. (1981) Cancer Res., 41: 2707–2713.
17. Ho, D. W. H. and Neil, B. L. (1977) Cancer Res., 37: 1640–1643.
18. Huang, A., Huang, L. and Kennel, S. J. (1980) J. Biol. Chem. 255: 8015–8018.
19. Leserman, L. D., Barbet, J. and Kourilsky, F. (1980) Nature, 288: 602–602.
20. Toorchen, D. and Topal, M. D. (1983) Carcinogenesis, 4: 1591–1597.
21. Agranoff, B. W. and Suomi, W. D. (1963) Biochem. Prep., 10: 46–51.
22. Prottey, C. and Hawthorne, J. N. (1967) Biochem. J., 105: 379–392.
23. Poorthuis, B. J. H. M. and Hostetler, K. Y. (1976) Biochim. Biophys. Acta, 431: 408–415.
24. ter Scheggett, J., van den Bosch, H., van Baak, M. A., Hostetler, K. Y. and Borst, P. (1971) Biochim. Biophys. Acta, 239: 234–242.
25. Rittenhouse, H. G., Seguin, E. B., Fisher, S. K. and Agranoff, B. W. (1981) J. Neurochem., 36: 991–999.
26. Olson, F., Hunt, C. A. Szoka, F. C., Vail, W. J. and Papahadjopoulos, D. (1979) Biochim, Biophys. Acta, 557: 9–23.
27. Szoka, F., and Papahadjopoulos, D. (1978) Proc. Nat. Acad. Sci. 75: 4194–4198.
28. Mayhew, E., Lazo, R., Vail, W. J., King, J., Green, A. M. (1984) 775: 169–175.
29. Kim, S., Turker, M., Chi, E., et al., Biochim. Biophys. Act, 728: 339:348.
30. Mayer, L. D., Hope, M. J. and Cullis, P. R. (1986) Biochim. Biophys. Acta, 858: 161–168.
31. Fukanga, M., Miller, M. M., Hostetler, K. Y. and Deftos, L. J. (1984) Endocrinol. 115: 757–761.
32. Brown, D. A., Malkin T. and Maliphant, G. K. (1955) J. Chem. Soc. (London) pp. 1584–1588.
33. Heath, T. D., Lopez, N. G., Piper, J. R., Montgomery, J. A., Stern, W. H. and Papahadjopoulos, D. (1986) Biochim. Biophys. Acta, 862: 72–80.
34. Bligh, E. and Dyer, W. (1959) Canad. J. Biochem. Physiol. 37:911–917.
35. Rosenthal, A. F. and Geyer, R. P.(1960) J. Biol. Chem. 235:2202.

What is claimed is:

1. A method for inhibiting a viral polymerase in a virally infected mammalian cell without killing the cell, said method comprising administering to a mammal in need thereof an effective antiviral amount of a liponucleotide compound comprising:
   an antiviral nucleoside analogue having an ability to selectively inhibit said viral polymerase enzyme without killing the cell; and
   a lipid moiety selected from the group consisting of glycerolipids having the structure

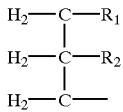

wherein said $R_1$ and $R_2$ independently have from 0 to 6 sites of unsaturation, and have the structure

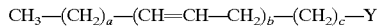

wherein the sum of a and c is from 1 to 23; and b is 0 to 6; and wherein Y is selected from the group consisting of —$CH_2$—O, —CH=CH—O—, —$CH_2$—S—, and —CH=CH—S—;
   wherein the antiviral nucleoside analogue is covalently bound to the lipid moiety through a mono-phosphate linkage to the 5' carbon of the pentose residue of the nucleoside analogue corresponding to the 5' carbon of naturally occurring nucleosides.

2. The method of claim 1, wherein said nucleoside analogue is selected from the group consisting of
   2',3'-dideoxycytidine;
   2',3'-dideoxyguanosine;
   2',3'-dideoxyadenosine;
   2',3'-dideoxyinosine;
   2,6-diaminopurine
   2',3'-dideoxyriboside;
   2',3'-didehydrothymidine;
   2',3'-didehydrocytidine carbocyclic;
   2',3'-didehydroguanosine;
   3'-azido-3'-deoxythymidine;
   3'-azido-3'-deoxyguanosine;
   2,6-diaminopurine-3'-azido-2',3'-dideoxyriboside;
   3'-fluoro-3'-deoxythymidine;
   3'-fluoro-2',3'-dideoxyguanosine;
   2',3'-dideoxy-2'-fluoro-ara-adenosine;
   2,6-diaminopurine-3'-fluoro-2',3'-dideoxyriboside;
   9-(4-hydroxy-1',2'-butadienyl) adenine;
   3-(4-hydroxy-1',2'-butadienyl) cytosine;
   9-(2-phosphonylmethoxyethyl) adenine;
   3-phosphonomethoxyethyl-2,6-diaminopurine;
   ganciclovir;
   3'-azido-2',3'-dideoxy-5-chlorouridine (AzddClU);
   3'-azido-2',3'-dideoxy-5-methylcytosine (AzddMeC);
   3'-azido-2',3'-dideoxy-5-methylcytosine-N4OH (AzddMeC N4OH);
   3'-azido-2',3'-dideoxy-5-methylcytosine-N4Me (AzddMeC N4Me);
   3'-azido-2',3'-dideoxy-5-ethyluridine (AzddEtU);
   3'-azido-2',3'-dideoxyuridine (AzddU);
   3'-azido-2',3'-dideoxycytosine (AzddC);
   3'-azido-2',3'-dideoxy-5-fluorocytosine (AzddFC);
   3'-azido-2',3'-dideoxy-5-bromouridine (AzddBrU);
   3'-azido-2',3'-dideoxy-5-fluorouridine (AzddTU);
   3'-fluoro-2',3'-dideoxy-5-chlorouridine (FddClU);
   3'-fluoro-2',3'-dideoxyuridine (3'FddU);
   3'-fluoro-2',3'-dideoxythymidine (3'FddT);
   3'-fluoro-2',3'-dideoxy-5-bromouridine (3'FddBrU);
   3'-fluoro-2',3'-dideoxy-5-ethyluridine (3'FddEtU);
   2',3'-dideoxy-2',3'-didehydrothymidine (D4T);
   2',3'-dideoxy-2',3'-didehydrocytidine (D4C);
   2',3'-dideoxy-2',3'-didehydro-5-methylcytidine (D4MeC);
   2',3'-dideoxy-2',3'-didehydroadenosine (D4A);
   5-fluoro-2',3'-dideoxycytidine (5FddC);
   2,6-diaminopurine-2',3'-dideoxyriboside (ddDAPR);
   5-methyl-2',3'-dideoxyadenosine (ddMeA);
   3'-azido-2',3'-dideoxy-diaminopurine ($N_3$ddDAPR);
   3'-azido-2',3'-dideoxyguanosine ($3N_3$ddG);
   3'-fluoro-2',3'-dideoxy-diaminopurine (3FddDAPR);
   3'-fluoro-2',3'-dideoxyguanosine (3FddG);
   3'-fluoro-2',3'-dideoxy-arabinofuranosyl-adenine (3Fddara-A);
   3'-fluoro-2',3'-dideoxyadenosine (3FddA); and
   2',3'-dideoxy-3'thiacytidine (3TC).

3. The method of claim 1 wherein said lipid moiety is selected from the group consisting of 1,2-O-alkylglycerols and 1,2-S-alkylglycerols.

4. The method of claim 1 wherein said lipid moiety is selected from the group consisting of 1-S-alkyl,2-O-alkylglycerols and 1-O-alkyl,2-S-alkylglycerols.

5. The method of claim 1 wherein said inhibition of said viral polymerase by said liponucleotide is greater than an inhibition of said viral polymerase by a corresponding free nucleoside.

6. The method of claim 1 wherein said liponucleotide comprises 1-S-dodecyl, 2-O-decylglycero-phospho-3'-azido-3'deoxythymidine.

7. The method of claim 1 wherein the antiviral nucleotide is 1-S-dodecyl,2-O-decylglycero-phospho-2',3'-dideoxycytosine.

8. The method of claim 1 wherein the antiviral nucleotide is 1-S-dodecyl,2-O-decylglycero-phospho-2',3'-didehydro, 2',3'-dideoxythymidine.

9. The method of claim 1 wherein the antiviral nucleotide is 1-S-dodecyl,2-O-decylglycero-phospho-2',3'-dideoxyinosine.

10. The method of claim 1 wherein the antiviral nucleotide is 1-S-dodecyl,2-O-decylglycero-phospho-9-[(1,3-dihydroxy-2-propoxy)methyl]guanine.

11. The method of claim 1 wherein the antiviral nucleotide is 1-S-dodecyl,2-O-decylglycero-phospho-2',3'-dideoxy-3'-thiacytidine.

* * * * *